US005955636A

United States Patent [19]
Kido et al.

[11] Patent Number: 5,955,636
[45] Date of Patent: Sep. 21, 1999

[54] PROCESS FOR PRODUCING 6-METHYL-3-HEPTEN-2-ONE AND 6-METHYL-2-HEPTANONE ANALOGUES, AND PROCESS FOR PRODUCING PHYTON OR ISOPHYTOL

[75] Inventors: Yoichi Kido; Noriaki Kumagai; Hideharu Iwasaki; Takashi Onishi, all of Ibaraki; Fuyuo Ueyama, Niigata, all of Japan

[73] Assignee: Kuraray Co., Ltd., Kurashiki, Japan

[21] Appl. No.: 08/887,260

[22] Filed: Jul. 2, 1997

[30] Foreign Application Priority Data

| Jul. 5, 1996 | [JP] | Japan | 8-195480 |
| Dec. 11, 1996 | [JP] | Japan | 8-352214 |
| Mar. 6, 1997 | [JP] | Japan | 9-051356 |

[51] Int. Cl.$^6$ ................................. C07C 45/61
[52] U.S. Cl. ............................. 568/390
[58] Field of Search ............................. 568/390

[56] References Cited

U.S. PATENT DOCUMENTS

| 2,485,989 | 10/1949 | Smith . | |
| 2,499,172 | 2/1950 | Smith . | |
| 2,792,421 | 5/1957 | Dalgleish . | |
| 2,809,215 | 10/1957 | Surmatis et al. . | |
| 3,082,260 | 3/1963 | Tedeschi et al. . | |
| 3,496,240 | 2/1970 | Sturzenegger . | |
| 4,146,581 | 3/1979 | Nissen | 568/390 |
| 4,701,562 | 10/1987 | Olson | 568/390 |

FOREIGN PATENT DOCUMENTS

| 0 008 741 | 3/1980 | European Pat. Off. . |
| 0 022 955 | 1/1981 | European Pat. Off. . |
| 0 765 853 | 4/1997 | European Pat. Off. . |
| 823 291 | 10/1951 | Germany . |
| 32-8616 | 12/1957 | Japan . |
| 49-25251 | 6/1974 | Japan . |
| 50-59308 | 5/1975 | Japan . |
| 907142 | 11/1959 | United Kingdom . |

OTHER PUBLICATIONS

R. Heilmann, et al., Bulletin De La Societe Chimique De France, pp. 112–118, "Recherches Sur Les Cetones Ethyleniques–V(*). Isomerie CIS–Trans Dans Les Cetones Du Type R.CH=CH.CO.Ch$_3$", 1957.

M. Mousseron–Canet, et al. Bulletin De La Societe Chimique De France, pp. 376–378, "Vitesses Relatives D'Epoxydation De Quelques Molecules Terpeniques", 1963.

U. Wannagat, et al., Monatshefte fur Chemie, vol. 125, No. 11, pp. 1159–1169, "Sila Perfumes and Isosteric Perfumes. 13. Isosteric Compounds According to the Hydride Principle of Grimm in the Linalool–Type of Odorous Compounds.", 1994.

A. Ofner, et al., Helvetica Chimica Acta., vol. XLII, No. VII, pp. 2577–2584, "Synthetisches Nerolidol Und Verwandte C$^{15}$–Alkohole", 1959.

S. Akutagawa, et al., Bulletin Of The Chemical Society Of Japan, vol. 51, No. 4, pp. 1158–1162, "Metal–Assisted Terenoid Synthesis. V.$^{1)}$ The Catalytic Trimerization of Isoprene to Trans–.β.–Farnesene and Its Synthetic Applications for Terpenoids", 1978.

Rene Heilmann, et al., Bull. Soc. Chim. Fr., pp. 112, 117 and 118, 1957, "Memoires Presentes A La Societe Chimique".

Kikumasa Sato, et al., Yuki Gosei Kagaku Kyokaisha, vol. 20, pp. 824–836, 1962, "Synthesis of Vitamin E (α–Tocopherol)".

Zh. Obshch., Chim., vol. 28, pp. 1444–1458, 1958.

Walter Kimel, et al., The Journal of Organic Chemistry, vol. 23, No. 2, pp. 153–157, Mar. 5, 1958, "Total Synthesis of Pseudoionone and an Isomeric Ketone".

Chem Ber, Rupe, 40, pp. 4764–4770, 1907.
CA:124:261425 CN1109462, Oct. 1995.
CA; 79:18094 DE2150992, Apr. 1973.
CA:84:43317, DE2412855, Oct. 1975.

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

Provided are a process for producing 6-methyl-3-hepten-2-one by cross aldol condensation carried out while each continuously adding to acetone, isovaleraldehyde and an aqueous alkali containing an alkaline substance; a process for producing a 6-methyl-2-heptanone analogue represented by Formula (1):

(1)

wherein n is an integer of 0 or 1 or more; which comprises allowing hydrogen, acetone and an aldehyde represented by Formula (2):

(2)

wherein n is as defined above; X and Y each represents a hydrogen atom or they are coupled together to form a carbon-carbon bond; and Z and W each represents a hydrogen atom or they are coupled together to form a carbon-carbon bond;

to react in the presence of an aqueous alkali containing an alkaline substance, and a hydrogenation catalyst; and a process for producing phyton or isophytol using the 6-methyl -3-hepten-2-one or the 6-methyl-2-heptanone analogue.

15 Claims, No Drawings

PROCESS FOR PRODUCING 6-METHYL-3-HEPTEN-2-ONE AND 6-METHYL-2-HEPTANONE ANALOGUES, AND PROCESS FOR PRODUCING PHYTON OR ISOPHYTOL

BACKGROUND OF THE INVENTION

1. Field of the Invention

This invention relates to a process for producing in an industrially simple manner 6-methyl-3-hepten-2-one and 6-methyl-2-heptanone analogues (e.g., 6-methyl-2-heptanone or 6,10-dimethyl-2-undecanone), which serve as materials for producing phyton or isophytol. This invention also relates to a process for producing phyton or isophytol from 6-methyl-3-hepten-2-one or the 6-methyl-2-heptanone analogue.

2. Description of the Related Art

As well known, phyton and isophytol are compounds useful as intermediates for producing biologically active substances such as vitamin E [see Yuki Gosei Kagaku Kyokaishi, 20, 824–836 (1962)] and can be produced by various processes. From the viewpoint of industrial application, a process is considered to be favored in which a ketone having 8 carbon atoms represented by the following Formula (I)

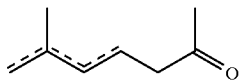

(I)

(the dotted line in the Formula means that one or two carbon-carbon double bond(s) can be present so long as the valence of carbon at the position indicated by such double bond(s) is satisfied) is used as an intermediate (hereinafter the ketone represented by Formula (I) is referred to as "C8 terpene ketone".

Here, in an instance, the whole process for producing phyton and isophytol where 6-methyl-5-hepten-2-one is used as the C8 terpene ketone will be shown by the following scheme.

Scheme:

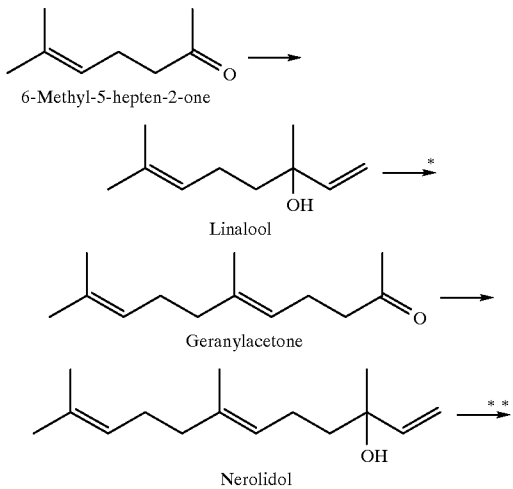

6-Methyl-5-hepten-2-one

Linalool

Geranylacetone

Nerolidol

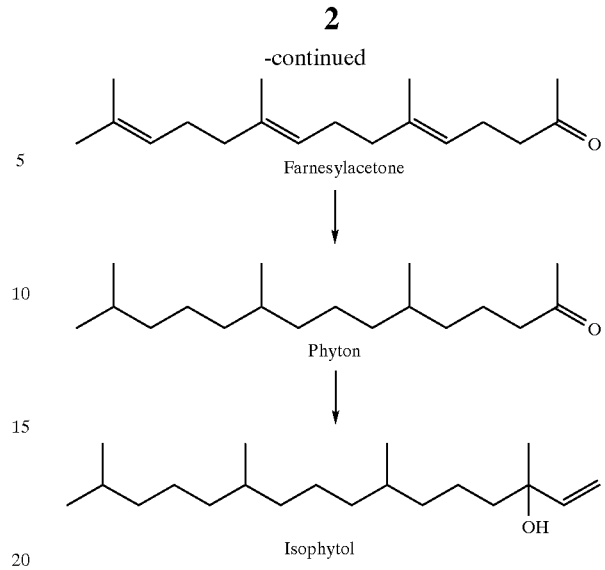

Farnesylacetone

Phyton

Isophytol

Thus, in the process for producing phyton or isophytol from the C8 terpene ketone, it basically proceeds that the principal carbon chain of the C8 terpene ketone is several times made longer by five carbons corresponding to the isoprene unit, followed by hydrogenation of the carbon-carbon double bond in the resulting compound. This basic procedure is not different whether or not unsaturated bonds are present, and at whatever positions they are, in the C8 terpene ketone. Accordingly, in the process for producing phyton or isophytol from C8 terpene ketone, how to produce the intermediate C8 terpene ketone with ease and at a low cost is one of important factors for the industrial application.

In this regard, as processes for producing the C8 terpene ketone, those shown below are known, for example.

Process (i): A process in which acetone, the starting material, is subjected to ethynylation by acetylene in the presence of an alkaline catalyst to form 3-methyl-1-butyn-3-ol and successive partial hydrogenation in the presence of a Lindlar catalyst, followed by reaction with diketene to form an ester derivative of acetoacetic acid. Thereafter, the ester thus formed is further subjected to Carroll rearrangement to produce 6-methyl-5-hepten-2-one [see, e.g., J. Org. Chem., 23, 153 (1958); Zh. Obshch. Chim., 28, 1444 (1958)].

Process (ii): A process in which isobutene, acetone and formaldehyde are allowed to react under conditions of a high temperature and a high pressure to give 6-methyl-6-hepten-2-one (see, e.g., German Patents No. 12 59 876 and No. 12 68 135 and U.S. Pat. No. 3,574,773).

Process (iii): A process in which prenyl chloride obtained by the reaction of isoprene with hydrogen chloride is allowed to react with acetone in the presence of an equimolar amount of an alkali based on the prenyl chloride to give 6-methyl-5-hepten-2-one (see, e.g., U.S. Pat. Nos. 3,983,175 and 3,984,475).

These processes for producing C8 terpene ketone, however, have problems as stated below.

The process (i) has a problem that it requires many steps resulting in a higher production cost. The process (ii) has a problem that it requires special manufacturing equipments because the reaction is carried out under conditions of a high temperature and a high pressure. In the process (iii), the use of an alkali in an equimolar amount based on the prenyl chloride results in the formation of a salt in a large quantity to make it necessary to take much labor for its disposal.

Accordingly, the present inventors have paid attention to 6-methyl-3-hepten-2-one as a compound that is different from the C8 terpene ketone and useful as a material for producing phyton or isophytol. This compound has an unsaturated bond at the α, β-position to the carbonyl group, so it is difficult to make the principal carbon chain of the 6-methyl-3-hepten-2-one longer by five carbons corresponding to the isoprene unit at a high conversion. However, when it is subjected to hydrogenation reaction, it can be converted into 6-methyl-2-heptanone, a kind of the C8 terpene ketone, a material for producing phyton and isophytol.

As processes for producing 6-methyl-3-hepten-2-one, processes comprising subjecting isovaleraldehyde and acetone to aldol condensation in the presence of an aqueous alkali as a basic catalyst are known. Such processes are known to include the following.

Process(iv): A process in which an equimolar mixture of isovaleraldehyde and acetone is stirred at 20 to 25° C. in the presence of an aqueous sodium hydroxide [see Nippon Kagaku Kaishi, 59, 224 (1938)].

Process(v): A process in which isovaleraldehyde is added in a mixture of acetone, diethyl ether and an aqueous sodium hydroxide while keeping the reaction temperature at 15° C. or below; the acetone being in an amount of 4 moles per mole of the isovaleraldehyde [see Bull. Soc. Chim. Fr., 112 (1957)].

In addition to the above, the following processes (vi) to (ix) are also known as processes for producing 6-methyl-3-hepten-2-one.

Process(vi): A process in which isovaleraldehyde and acetone are heated in the absence of a catalyst under pressure or in a sealed vessel to carry out reaction at a high temperature (300° C.) and a high pressure (270 kg/cm$^2$) (See British Patent No. 1,246,698).

Process(vii): A process in which isovaleraldehyde and acetone are allowed to react in the presence of zinc oxide at 180° C. under 35 atmospheric pressure (see U.S. Pat. No. 4,005,147).

Process(viii): A process in which isoamyl alcohol and acetone are condensed in the presence of an aluminum isopropoxide [see Nippon Kagaku Kaishi, Vol. 81, p.675 (1960)].

Process(ix): A process in which acetylacetylene and truisobutylborane are allowed to react in the presence of oxygen [see J. Am. Chem. Soc., 92, 3503 (1970)].

However, the processes (vi) and (vii) both are carried out under conditions of a high temperature and a high pressure, so they require special manufacturing equipment. Moreover, the conversion of isovaleraldehyde is as low as 24% and 73%, respectively, which is not satisfactory. The process (viii) must use expensive aluminum isopropoxide in an equimolar amount based on the isoamyl alcohol, and the process (ix) must use very expensive acetylacetylene and triisobutylborane. Thus, the processes (vi) to (ix) can not be estimated industrially advantageous in view of manufacturing equipment and cost of materials.

In contrast, the processes comprising subjecting isovaleraldehyde and acetone to aldol condensation in the presence of an aqueous alkali have an advantage that the reaction can be carried out under mild conditions, using inexpensive materials. The process (iv), however, can give 6-methyl-3-hepten-2-one, the aldol condensate, only in a 35 to 40% yield at most. Also, the process (v) mainly forms 6-methyl-4-hydroxyheptan-2-one, and requires successive dehydration reaction in order to obtain the yield of the 6-methyl-3-hepten-2-one. In addition, the yield of the 6-methyl-3-hepten-2-one thus obtained is 51%, which is not satisfactory. Moreover, the process (v) must use acetone in excess, so it is not industrially advantageous in view of the necessity for recovering the excessive acetone and the volumetric efficiency of reaction.

The 6-methyl-2-heptanone formed by hydrogenation of 6-methyl-3-hepten-2-one is not only useful as a material for producing phyton and isophytol as previously stated, which are intermediates for producing vitamin E, but also useful as a material for producing perfumes such as tetrahydrolinalool and dihydrogeraniol [see, e.g., Bull. Soc. Chim. Fr., 1586 (1955)].

As conventional processes for producing 6-methyl-2-heptanone, processes (x) to (xv) shown below are known.

Process(x): A process in which an isoamyl halide and an acetoacetic acid ester are subjected to condensation reaction under alkaline conditions, followed by hydrolysis and then decarboxylation (see, e.g., Wagner, "SYNTHETIC ORGANIC CHEMISTRY", p.327, John Wiley & Sons, Inc.).

Process(xi): A process in which 6-methyl-5-hepten-2-one or 6-methyl-3,5-heptadien-2-one is subjected to hydrogenation in the presence of a hydrogenation catalyst such as Pd or Ni [see, e.g., European Patent No. 34,804; J. Org. Chem., 42, 1709 (1977); Izv. Akad. Nauk. SSSR. Khim., 10, 2381 (1972)].

Process(xii): A process in which 6-methyl-2-heptanol is oxidized [see, e.g., Recl. Trav. Chim. Pays-Bas, 28, 116 (1909)].

Process(xiii): A process in which 6-methyl-5-hepten -2-ol is treated with a mixture of 85% phosphoric acid and phosphorus pentoxide [see, Bull. Soc. Chim. Fr., 1799 (1963)].

Process(xiv) A process in which methyl vinyl ketone is subjected to 1,4-addition with an isobutyl magnesium halide [see, Bull. Chem. Soc. Jpn., 38, 29 (1965)].

Process(xv): A process in which isovaleraldehyde and acetone are allowed to react under a stream of hydrogen, in the presence of a catalyst comprised of a metal oxide and a metal belonging to Group VIII of the periodic table (See U.S. Pat. Nos. 4,146,581 and 4,212,825).

The above processes, however, have problems as discussed below.

In the process (x), a base is used in an equimolar amount based on the acetoacetic acid ester, so a salt is formed in a large quantity to require much labor for its disposal, resulting in a high cost for the production of the 6-methy-2-heptanone.

In the processes (xi) and (xii), the production of 6-methyl-5-hepten-2-one, 6-methyl-3,5-heptadien-2-one or 6-methyl-2-heptanol, the starting material, is complicated because many steps are required from inexpensive and readily available materials.

In the process (xiii), not only the production of the 6-methyl-5-hepten-2-ol is complicated because many steps are required from inexpensive and readily available materials, but also the 85% phosphoric acid and phosphorus pentoxide are used in a large quantity to require much labor for the disposal of waste water.

In the process (xiv), the isobutyl magnesium halide is used in an equimolar amount based on the methyl vinyl ketone, so a salt is formed in a large quantity to require much labor for its treatment, resulting in a high production cost. Moreover, methyl vinyl ketone, one of the materials, has so high a tendency to polymerization and also the other isobutyl magnesium halide is so sensitive to water and oxygen that they must be handled with care.

In the process (xv), the reaction is carried out under conditions of a high temperature and a high pressure, so it requires a special manufacturing equipment.

The above conventional processes for producing 6-methyl-2-heptanone have subjects to be settled in view of production cost and manufacturing equipment. Thus, no industrially advantageous process has been established for producing the 6-methyl-2-heptanone.

Besides the 6-methyl-2-heptanone, as intermediates for producing phyton or isophytol, one may contemplate making use of 6-methyl-2-heptanone analogues having 6-methyl-2-heptanon-7-yl residual groups, such as 6,10-dimethyl-2-decanone and 6,10,14-trimethyl-5,9-pentadecadien-2-one. Production processes for these, however, also is considered to have similar problems.

SUMMARY OF THE INVENTION

The present invention aims at solving the problems discussed above. Accordingly, a first object of the present invention is to provide a process for producing 6-methyl-3-hepten-2-one in an industrially advantageous manner.

A second object of the present invention is to provide a process for producing phyton or isophytol in an efficient and industrially simple manner; the process including a process for producing 6-methyl-2-heptanone.

A third object of the present invention is to provide a process for producing, in an efficient and industrially simple manner, 6-methyl-2-heptanone and analogues thereof (e.g., 6-methyl-2-heptanone and 6,10-diemthyl-2-undecanone; the 6-methyl-2-heptanone and analogues thereof are herein simply called "6-methyl-2-heptanone analogues" as a whole) which can be used as materials for producing phyton or isophytol.

The above first object can be achieved by a production process according to a first embodiment of the present invention, i.e., a process for producing 6-methyl-3-hepten-2-one, comprising the step of subjecting isovaleraldehyde and acetone to cross aldol condensation, wherein the cross aldol condensation is carried out while each continuously adding to the acetone the isovaleraldehyde and an aqueous alkali containing an alkaline substance, to give 6-methyl-3-hepten-2-one.

The second object of the present invention can be achieved by a production process according to a second embodiment of the present invention, i.e., a process for producing phyton, comprising the following steps (a) to (g):

Step (a): subjecting isovaleraldehyde and acetone to cross aldol condensation while each continuously adding to the acetone the isovaleraldehyde and an aqueous alkali containing an alkaline substance, to form 6-methyl-3-hepten-2-one according to the production process of the first embodiment;

step (b): subjecting the 6-methyl-3-hepten-2-one obtained in the step (a), to hydrogenation to form 6-methyl-2-heptanone;

step (c): allowing the 6-methyl-2-heptanone obtained in the step (b) to react with a vinyl magnesium halide to effect vinylation, or subjecting the 6-methyl-2-heptanone to ethynylation and successive partial hydrogenation, to form 3,7-dimethyl-1-octen-3-ol;

step (d): allowing the 3,7-dimethyl-1-octen-3-ol obtained in the step (c) to react with diketene or an acetoacetic acid ester to form an acetoacetic acid ester of 3,7-dimethyl-1-octen-3-ol and subjecting the resultant ester to Carroll rearrangement, or allowing the 3,7-dimethyl-1-octen-3-ol to react with an isopropenyl alkyl ether to form an isopropenyl ether of 3,7-dimethyl-1-octen-3-ol and subjecting the resultant ether to Claisen rearrangement, to give 6,10-dimethyl-5-undecen-2-one;

step (e): allowing the 6,10-dimethyl-5-undecen-2-one obtained in the step (d) to react with a vinyl magnesium halide to effect vinylation, or subjecting the 6,10-dimethyl-5-undecen-2-one to ethynylation and successive partial hydrogenation, to form 3,7,11-trimethyl-1,6-dodecadien-3-ol;

step (f): allowing the 3,7,11-trimethyl-1,6-dodecadien-3-ol obtained in the step (e) to react with diketene or an acetoacetic acid ester to form an acetoacetic acid ester of 3,7,11-trimethyl-1,6-dodecadien-3-ol and subjecting the resultant ester to Carroll rearrangement, or allowing the 3,7,11-trimethyl-1,6-dodecadien-3-ol to react with an isopropenyl alkyl ether to form an isopropenyl ether of 3,7,11-trimethyl-1,6-dodecadien-3-ol and subjecting the resultant ether to Claisen rearrangement, to give 6,10,14-trimethyl-5,9-pentadecadien-2-one; and step (g): subjecting the 6,10,14-trimethyl-5,9-pentadecadien-2-one obtained in the step (f) to hydrogenation to form phyton.

In this process, isophytol can be obtained by providing the step (step (h)) of allowing the phyton formed in the step (g) to react with a vinyl magnesium halide to effect vinylation, or by subjecting the phyton to ethynylation and successive partial hydrogenation, to form isophytol.

The third object of the present invention can be achieved by a production process according to a third embodiment of the present invention, i.e., a process for producing a 6-methyl-2-heptanone analogue represented by Formula (1), including the 6-methyl-2-heptanone:

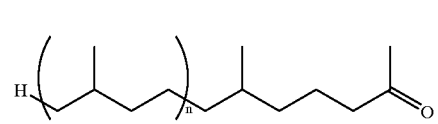

wherein n is an integer of 0 or 1 or more;

the process comprising the step of allowing hydrogen, acetone and an aldehyde represented by Formula (2):

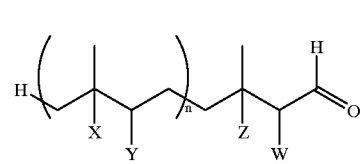

wherein n is as defined above; X and Y each represents a hydrogen atom or they are coupled together to form a carbon-carbon bond; and Z and W each represents a hydrogen atom or they are coupled together to form a carbon-carbon bond; to react in the presence of an aqueous alkali containing an alkaline substance, and a hydrogenation catalyst.

These and other objects, features and benefits of the present invention are described in or will become apparent from the following detailed description of the invention.

DETAILED DESCRIPTION OF THE INVENTION

The present invention will be described below in detail.

The present inventors made studies on the reaction conditions in the aldol condensation of isovaleraldehyde with acetone in the presence of an aqueous alkali to achieve the above first object.

More specifically, the first embodiment of the present invention is a process for producing 6-methyl-3-hepten-2-one by subjecting isovaleraldehyde and acetone to cross aldol condensation in the presence of an aqueous alkali, and is characterized by carrying out the reaction while each continuously adding to the acetone the isovaleraldehyde and an aqueous alkali containing an alkaline substance.

It is commonly known as aldol reaction that carbonyl compounds such as aldehydes or ketones undergo condensation in the presence of a basic catalyst to form aldols or ketols. For example, isovaleraldehyde or acetone readily undergoes self aldol condensation in the presence of a basic catalyst to form the corresponding aldol or ketol, respectively, followed by intramolecular dehydration to give an $\alpha$, $\beta$-unsaturated carbonyl compound as an aldol condensate (see, e.g., "ORGANIC REACTIONS" Vol. 16, pages 88 and 112, John Wiley & Sons, Inc.). Such an $\alpha$, $\beta$-unsaturated carbonyl compound can be converted into further condensate easily by the aldol reaction.

Aldol reaction between different two carbonyl compounds is also known as cross aldol condensation. In the cross aldol condensation, a variety of products are formed in most cases, and it is usually difficult to selectively obtain an aldol condensate in which the two different carbonyl compounds have condensed one by one (hereinafter referred to as "cross aldol condensate"). Accordingly, in the cross aldol condensation, in order to improve the selectivity of the cross aldol condensate on the basis of one of the two different carbonyl compounds, the other carbonyl compound is commonly used in excess. However, in the case of aldol condensation, which is conventionally carried out, the basic catalyst is present in the reaction mixture at the start of the reaction, so that the formation of a self aldol condensate of the excessive carbonyl compound is involved to reduce the yield of the desired cross aldol condensate, make it difficult to isolate the cross aldol condensate and also result in contamination by impurities in a large quantity.

Now, in the first embodiment of the present invention, on the aldol condensation of isovaleraldehyde with acetone, the isovaleraldehyde and an aqueous alkali are each continuously added to the acetone. This makes it possible to produce 6-methyl-3-hepten-2-one in a high yield, to prevent the contamination by impurities and to isolate the desired compound with ease. The reason why such effects can be attained is seemed to be that, since the reaction is carried out while adding isovaleraldehyde to acetone, the acetone can be present in great excess to the isovaleraldehyde in the reaction mixture during the greater period of the reaction, so that the selectivity of 6-methyl-3-hepten-2-one on the basis of isovaleraldehyde is improved. Moreover, since an aqueous alkali, the catalyst, is also continuously added, the concentration of alkali in the reaction mixture can be controlled to be as low as possible at the stage immediately after the reaction is initiated. In the meantime, as the addition of isovaleraldehyde proceeds and the reaction of isovaleraldehyde with acetone proceeds, the concentration of alkali increases with a decrease in the concentration of acetone in the reaction mixture. Thus, it becomes possible to run the reaction to the completion with ease, and consequently to prevent the reduction of selectivity to 6-methyl-3-hepten-2-one by the runaway of the reaction.

There are no particular limitations on the ratio of the acetone to the isovaleraldehyde which are used in the first embodiment of the present invention. In order to improve the selectivity to 6-methyl-3-hepten-2-one on the basis of isovaleraldehyde, which is more expensive, the acetone is preferably used within the range of from 0.5 to 3 moles per mole of the isovaleraldehyde. From the viewpoint of improving the volumetric efficiency of the reaction, the acetone is used more preferably within the range of from 0.8 to 2 moles, and particularly preferably within the range of from 0.9 to 1.2 moles, per mole of the isovaleraldehyde.

The alkaline substance used in the first embodiment of the present invention includes, e.g., alkali metal hydroxides such as sodium hydroxide and potassium hydroxide, alkaline-earth metal hydroxides such as barium hydroxide and calcium hydroxide, alkali metal carbonates such as potassium carbonate, and amine compounds such as 1,5-diazabicyclo[5.4.0]undecene-5 (DBU) and piperidine. In particular, alkali metal hydroxides and alkaline-earth metal hydroxides are preferred as the alkaline substance.

The alkaline substance can be used alone or in combination of two or more types.

The alkaline substance can be used in an amount of usually from 0.001 to 0.2 mole per mole of isovaleraldehyde, and, from the viewpoints of reaction rate and production cost, preferably from 0.01 to 0.1 mole per mole of isovaleraldehyde.

The alkaline substance can be used in the aqueous alkali in a concentration of usually from 0.5 to 30% by weight, and preferably from 1 to 10% by weight.

The cross aldol condensation according to the first embodiment of the present invention is usually carried out in the absence of an organic solvent. The organic solvent, however, can be used so long as the reaction is not adversely affected. Usable organic solvents include, e.g., aliphatic alcohols such as methanol, ethanol, propanol, isopropanol, n-butanol, s-butanol and t-butanol; ethers such as tetrahydrofuran, 1,4-dioxane, diethyl ether, diisopropyl ether and di-n-butyl ether; and hydrocarbons such as hexane, heptane, octane, benzene, toluene and xylene.

The cross aldol condensation according to the first embodiment of the present invention can preferably be carried out in an atmosphere of inert gas such as nitrogen or argon.

The cross aldol condensation according to the first embodiment of the present invention is usually carried out by each continuously adding isovaleraldehyde and an aqueous alkali in a reaction vessel equipped with a stirrer and in which acetone has been charged. The term "continuously add" referred to in the first embodiment of the present invention means that the isovaleraldehyde and the aqueous alkali are fed, and, so long as the object of the invention is achieved, embraces an embodiment that isovaleraldehyde and an aqueous alkali are added in parts by several times.

Usually, the addition of isovaleraldehyde and that of an aqueous alkali are started simultaneously. Isovaleraldehyde can be added in advance so long as its amount is within the ⅕ mole of the acetone. As for the aqueous alkali, by-products due to self aldol condensation of the acetone may increase to reduce the selectivity to the 6-methyl-3-hepten-2-one, if it is added in advance in a large quantity. It, however, can be added in advance so long as the amount of alkaline compound is within about 1 mole % based on the acetone.

Adding the mixture of isovaleraldehyde and an aqueous alkali to acetone is not preferable because the self aldol condensation of isovaleraldehyde may take place to reduce the selectivity to 6-methyl-3-hepten-2-one.

Usually, the addition of isovaleraldehyde and that of an aqueous alkali are controlled so that the both are completed simultaneously. However, either addition can be completed in advance so long as it is not completed too early.

The time for the addition of isovaleraldehyde and an aqueous alkali depends on the kind, concentration and so forth of an alkaline substance used. They can usually be added for 30 minutes to 10 hours.

The cross aldol condensation according to the first embodiment of the present invention is usually carried out at a temperature ranging from −20 to 100° C., and preferably from 40 to 80° C. in order to control the reaction rate at a practical level and to improve the selectivity to 6-methyl-3-hepten-2-one.

The cross aldol condensation according to the first embodiment of the present invention can be carried out at under normal pressure or elevated pressure.

The cross aldol condensation according to the first embodiment of the present invention proceeds at the same time the addition of isovaleraldehyde and an aqueous alkali is started, and is usually completed within 5 hours after their addition is completed.

In the course the addition of isovaleraldehyde and an aqueous alkali and in the course the reaction is run to the completion, the reaction mixture is preferable to be thoroughly stirred.

After the reaction is completed, 6-methyl-3-hepten-2-one, the product, can be isolated by a known method, e.g., a method in which a reaction mixture is subjected to the removal of the aqueous layer, followed by distillation, or a method in which the product is extracted with an organic solvent from a reaction mixture followed by evaporation of the organic solvent under normal pressure or reduced pressure.

Such an organic solvent may include, e.g., hydrocarbons such as toluene, benzene and cyclohexane, and halogenated hydrocarbons such as methylene chloride, chloroform, carbon tetrachloride and dichloroethane.

According to the first embodiment of the present invention, the 6-methyl-3-hepten-2-one, which is the cross aldol condensate of isovaleraldehyde with acetone, can be produced in a good yield, using inexpensive materials and by a simple procedure without requiring any special manufacturing equipment. Also, according to the first embodiment of the present invention, the 6-methyl-4-hydroxyheptan-2-one, which is an aldol adduct of isovaleraldehyde with acetone, is formed usually in an amount of as small as 5 mole% based on the 6-methyl-3-hepten-2-one. Thus the 6-methyl-3-hepten-2-one can be selectively obtained.

Next, the second embodiment of the present invention that achieves the second object of the present invention will be described below.

The second embodiment of the present invention is a process for producing phyton in which the production process of the first embodiment is included as the first step, and comprises the following steps:

Step (a): the step of subjecting isovaleraldehyde and acetone to cross aldol condensation while each continuously adding to the acetone the isovaleraldehyde and an aqueous alkali containing an alkaline substance, to form 6-methyl-3-hepten-2-one identical with the production process of the first embodiment;

step (b): the step of subjecting the 6-methyl-3-hepten-2-one obtained in the step (a), to hydrogenation to form 6-methyl-2-heptanone;

step (c): the step of allowing the 6-methyl-2-heptanone obtained in the step (b) to react with a vinyl magnesium halide to effect vinylation, or subjecting the 6-methyl-2-heptanone to ethynylation and successive partial hydrogenation, to form 3,7-dimethyl-1-octen-3-ol;

step (d): the step of allowing the 3,7-dimethyl-1-octen-3-ol obtained in the step (c) to react with a diketene or an acetoacetic acid ester to form an acetoacetic acid ester of 3,7-dimethyl-1-octen-3-ol and subjecting the resultant ester to Carroll rearrangement, or allowing the 3,7-dimethyl-1-octen-3-ol to react with an isopropenyl alkyl ether to form an isopropenyl ether of 3,7-dimethyl-1-octen-3-ol and subjecting the resultant ether to Claisen rearrangement, to give 6,10-dimethyl-5-undecen-2-one;

step (e): the step of allowing the 6,10-dimethyl-5-undecen-2-one obtained in the step (d) to react with a vinyl magnesium halide to effect vinylation, or subjecting the 6,10-dimethyl-5-undecen-2-one to ethynylation and successive partial hydrogenation, to form 3,7,11-trimethyl-1,6-dodecadien-3-ol;

step (f): the step of allowing the 3,7,11-trimethyl-1,6-dodecadien-3-ol obtained in the step (e) to react with a diketene or an acetoacetic acid ester to form an acetoacetic acid ester of 3,7,11-trimethyl-1,6-dodecadien-3-ol and subjecting the resultant ester to Carroll rearrangement, or allowing the 3,7,11-trimethyl-1,6-dodecadien-3-ol to react with an isopropenyl alkyl ether to form an isopropenyl ether of 3,7,11-trimethyl-1,6-dodecadien-3-ol and subjecting the resultant ether to Claisen rearrangement, to give 6,10,14-trimethyl-5,9-pentadecadien-2-one; and step (g): the step of subjecting the 6,10,14-trimethyl-5,9-pentadecadien-2-one obtained in the step (f) to hydrogenation to form phyton (6,10,14-trimethylpentadecan-2-one).

The production process according to the second embodiment of the present invention can also be a process for producing isophytol by providing, subsequent to the above step (g);

step (h): the step of allowing the phyton formed in the step (g) to react with a vinyl magnesium halide to effect vinylation, or by subjecting the phyton to ethynylation and successive partial hydrogenation, to form isophytol.

In the second embodiment of the present invention, the 6-methyl-3-hepten-2-one obtained in the step (a), identical with the production process according to the first embodiment of the present invention, is quantitatively converted into 6-methyl-2-heptanone by the hydrogenation in the step (b). The 6-methyl-2-heptanone, a kind of the C8 terpene ketones, obtained through the step (a) and the subsequent step (b) can be produced from inexpensive and readily available materials under mild production conditions and in a higher yield than the C8 terpene ketones obtained by the processes (i) to (iii) and (x) to (xv), so that the phyton and isophytol can be produced in an industrially advantageous manner.

The process for producing phyton or isophytol according to the second embodiment of the present invention will be detailed below in the order of steps.

Step (a):

In the step (a), isovaleraldehyde and acetone are subjected to cross aldol condensation while each continuously adding to the acetone the isovaleraldehyde and the aqueous alkali to form 6-methyl-3-hepten-2-one. This step (a) is identical with the production process according to the first embodiment of the present invention, thus all the details given for the latter are common to the former.

Step (b):

In the step (b), the 6-methyl-3-hepten-2-one obtained in the step (a) is subjected to hydrogenation to form 6-methyl-2-heptanone.

The 6-methyl-3-hepten-2-one obtained by the cross aldol condensation in the step (a) has a carbon-carbon double bond at the α, β-position to the carbonyl group, so, if left as it is, it is difficult to make the principal carbon chain of the 6-methyl-3-hepten-2-one longer by five carbons in a good selectivity through the steps (c) and (d) described later. Accordingly, in view of industrial application, the 6-methyl-3-hepten-2-one should be converted into the 6-methyl-2-heptanone by hydrogenation, prior to the subsequent steps.

This hydrogenation can be carried out by a known method that can convert a carbon-carbon double bond to a saturated carbon-carbon bond. For example, the 6-methyl -3-hepten-2-one can be hydrogenated generally in an autoclave, in the presence of a conventional hydrogenation catalyst comprised of palladium, platinum, Raney nickel, Raney cobalt or the like (preferably palladium on carbon, without solvent or in a solvent including hydrocarbons, alcohols, ethers, ketones, esters and carboxylic acids, under hydrogen pressure of from 1 to 100 $kg/cm^2$, and preferably from 1 to 20 $kg/cm^2$, and at a temperature of from 15 to 150° C., and preferably from 30 to 130° C. The reaction time can be appropriately set in accordance with the kind of the solvent used or the hydrogen pressure.

Here the hydrogenation catalyst is used in an amount of generally from 0.01 to 10% by weight, preferably from 0.03 to 3% by weight, based on the weight of 6-methyl-3-hepten-2-one.

After the reaction is completed, 6-methyl-2-heptanone can be isolated from the reaction mixture by a conventional method, e.g., by distillation.

Step (c)

In the step (c), 3,7-dimethyl-1-octen-3-ol is formed from the 6-methyl-2-heptanone obtained in the step (b), by adding a vinyl group ($—CH_2=CH_2$) to the carbonyl group at its terminal. As a method for the step (c), either method is selected from a method in which the 6-methyl-2-heptanone is allowed to react with a vinyl magnesium halide to effect vinylation, or a method in which the 6-methyl-2-heptanone is subjected to ethynylation and successive partial hydrogenation. For the industrial application, it is more advantageous to effect the latter ethynylation and successive partial hydrogenation.

In the former method, in which the 6-methyl-2-heptanone is allowed to react with a vinyl magnesium halide, 3,7-dimethyl-1-octen-3-ol can be obtained by, e.g., adding the 6-methyl-2-heptanone to a vinyl magnesium halide prepared from a vinyl halide such as vinyl chloride or vinyl bromide and metal magnesium in a solvent such as tetrahydrofuran or diethyl ether, in such an amount of from 0.5 to 2 moles per mole of the vinyl magnesium halide to carry out reaction at a temperature of usually from −10 to 55° C., and preferably from 0 to 40° C., followed by hydrolysis using dilute aqueous sulfuric acid, a saturated aqueous ammonium chloride or the like.

In the latter method, in which the 6-methyl-2 -heptanone is subjected to ethynylation and successive partial hydrogenation, the 6-methyl-2-heptanone is first ethynylated by a conventional method to form 3,7-dimethyl-1-octyn-3-ol, having 10 carbon atoms and having a carbon-carbon triple bond at the terminal. Here, the ethynylation can be carried out by a known process as a process in which ketones are ethynylated to form compounds having a propargyl alcohol structure (see U.S. Pat. Nos. 3,082,260 and 3,496,240; Japanese Patent Application Laid-open No. sho50-59308, etc.). When the ethynylation is carried out in a small scale, it is also possible to use a method with an acetylide of an alkali metal such as lithium, sodium or potassium or an alkaline earth metal such as calcium [see Org. Synth., 3, 416 (1955)] or a method with an ethynyl magnesium halide [see Org. Synth., 4, 792 (1963)].

When the ethynylation is carried out in an industrial scale, it is suitable to use, as described below, a method of direct ethynylation by acetylene in the presence of a strong base, because 3,7-dimethyl-1-octyn-3-ol can be produced at a low production cost and the work up can be made easily. This direct ethynylation is carried out by a process in which the 6-methyl-2-heptanone is allowed to react with acetylene, usually in an amount of from 1 to 10 moles per mole of the former, at −30° C. to 30° C. for 1 hour to 20 hours. The reaction is carried out under conditions where a strong base containing an alkali metal such as sodium or potassium (e.g., a hydroxide of the alkali metal, an alkali metal alcoholate or an alkali metal amide) is present in a catalytic amount, and in an organic solvent which does not inhibit the reaction such as N,N-dimethylformamide, dimethyl sulfoxide, N-methylpyrrolidone, tetrahyrofuran, dimethyl ether, diethyl ether, methyl ethyl ether, anisole or dioxane, or liquid ammonia, or a mixed solvent of these. After the reaction, the acetylene is purged off from the reaction vessel, and 3,7-dimethyl-1-octyn-3-ol is obtained as a residue.

Next, the 3,7-dimethyl-1-octyn-3-ol obtained as described above is partially hydrogeneated to give the 3,7-dimethyl-1-octen-3-ol. This partial hydrogenation intends to selectively reduce the carbon-carbon triple bond to a carbon-carbon double bond, and methods therefor are known per se. As methods for selectively reduce carbon-carbon triple bonds to the carbon-carbon double bonds, a method in which a hydrogenating agent such as lithium aluminum hydride is used [see J. Chem. Soc., 1854 (1954)] and a method in which a propargyl type alcohol is catalytically reduced in the presence of a hydrogenation catalyst in a solvent of a hydrocarbon such as n-hexane, n-heptane, octane, benzene, toluene or xylene and/or an alcohol such as, methanol, ethanol or propanol [see Org. Synth., 5, 880 (1973)] can be exemplified.

From an industrial viewpoint, the latter method is preferred. The hydrogenation of 3,7-dimethyl-1-octen-3-ol is carried out, e.g., in an atmosphere of hydrogen, at a hydrogen pressure of from normal pressure to 50 $kg/cm^2$, and preferably from 2 to 20 $kg/cm^2$, and at a temperature of from 0 to 130° C., and preferably from 20 to 80° C. As the hydrogenation catalyst, a metal such as nickel, cobalt, palladium, platinum, rhodium or iridium or a compound containing these metal can be used. These can be supported on carriers such as activated carbon, barium sulfonate and calcium carbonate. In particular, in the present invention, a Lindlar catalyst comprising palladium supported on calcium carbonate is especially preferable.

After the reaction is completed, 3,7-dimethyl-1-octen-3-ol can be isolated from the reaction mixture by a conventional method, e.g., by distillation.

Step (d):

In the step (d), 6,10-dimethyl-5-undecen-2-one is formed from the 3,7-dimethyl-1-octen-3-ol obtained in the step (c). As a method for the step (d), either method is selected from a method in which the 3,7-dimethyl-1-octen -3-ol is allowed to react with diketene or an acetoacetic acid ester to form an acetoacetic acid ester of 3,7-dimethyl-1-octen-3-ol and subjecting the resultant ester to Carroll rearrangement, or a method in which the 3,7-dimethyl-1-octen-3-ol is allowed to react with an isopropenyl alkyl ether to form an isopropenyl ether of 3,7-dimethyl-1-octen-3-ol and subjecting the resultant ether to Claisen rearrangement.

In the former method, which employs Carroll rearrangement, first, the acetoacetic acid ester of 3,7-dimethyl-1-octen-3-ol is formed by allowing 3,7-dimethyl-1-octen-3-ol to react with diketene usually in an amount of from 0.8 to 2 moles, and preferably from 0.9 to 1.2 moles, per mole of the former. In this instance, the acetoacetic acid ester can be formed by merely making the 3,7-dimethyl-1-octen-3-ol contact with the diketene without a solvent or in an organic solvent which does not inhibit the reaction such as hydrocarbons or ethers. If necessary, the reaction can be conducted with heating to from 50 to 100° C. Also, an amine such as triethylamine or pyridine can be added in a catalytic amount to the reaction mixture, which accelerates the rate of esterification and improves the yield of the acetoacetic acid ester of 3,7-dimethyl-1-octen-3-ol.

Next, the acetoacetic acid ester of 3,7-dimethyl-1 -octen-3-ol thus obtained is heated to usually from 130 to 180° C., and preferably from 150 to 180° C., in order to make the Carroll rearrangement (rearrangement and successive decarboxylation) proceed to give 6,10-dimethyl-5-undecen-2-one. At this step, an aluminum alkoxide such as aluminum isopropoxide can be added in a catalytic amount of the reaction mixture, which improves the yield of the 6,10-dimethyl-5-undecen-2-one.

Also 6,10-dimethyl-5-undecen-2-one can be obtained from the 3,7-dimethyl-1-octen-3-ol and diketene in one pot by mixing the reactants necessary for the above two-step reaction (esterification and Carroll rearrangement) all at once and controlling the reaction temperature.

In the foregoing, the reaction can be carried out under similar conditions when an acetoacetic acid ester such as methyl acetoacetate or ethyl acetoacetate is used in place of the diketene, and the similar results as in the foregoing can be obtained. These reactions and their mechanism are described in the literature [See e.g., J. Chem. Soc. 704 (1940); Japanese Patent Publications No. sho32-8616 and No. sho49-25251; British Patent No. 907,142, etc.]

Meanwhile, in the latter method, which employs Claisen rearrangement, the mixture of 3,7-dimethyl-1-octen-3-ol and an isopropenyl alkyl ether such as isopropenyl methyl ether or isopropenyl ethyl ether in an amount of from 0.5 to 10 moles, and preferably from 0.8 to 3 moles, per mole of the former are heated at a temperature of from 50 to 200° C., and preferably from 100 to 200° C., in the presence of an acidic catalyst such as phosphoric acid, sulfuric acid, oxalic acid or trichloroacetic acid to effect isopropenyl etherification of the 3,7-dimethyl-1-octen-3-ol, and the resultant ether is converted into 6,10-dimethyl-5-undecen-2-one by Claisen rearrangement [see, e.g., Japanese Patent Publication No. sho40-23328].

After the reaction is completed, 6,10-dimethyl-5-undecen-2-one can be isolated from the reaction mixture by a conventional method, e.g., by distillation.

Step (e):

In the step (e), 3,7,11-trimethyl-1,6-dodecadien-3-ol is formed from the 6,10-dimethyl-5-undecen-2-one obtained in the step (d), by adding a vinyl group to the carbonyl group at its terminal. As a method for the step (e), either method is selected from a method in which the 6,10-dimethyl-5-undecen-2-one is allowed to react with a vinyl magnesium halide to effect vinylation, or a method in which the 6,10-dimethyl-5-undecen-2-one is subjected to ethynylation and successive partial hydrogenation.

From the industrial application, the latter method in which the 6,10-dimethyl-5-undecen-2-one is subjected to ethynylation and successive partial hydrogenation is more advantageous.

This step (e) can be carried out following the procedure described in the step (c).

More specifically, in the former method, in which 6,10-dimethyl-5-undecen-2-one is allowed to react with a vinyl magnesium halide, the 3,7,11-trimethyl-1,6-dodecadien-3-ol can be obtained by, e.g., adding the 6,10-dimethyl-5-undecen-2-one to a vinyl magnesium halide prepared from a vinyl halide such as vinyl chloride or vinyl bromide and metal magnesium in a solvent such as tetrahydrofuran or diethyl ether, in such an amount of from 0.5 to 2 moles per mole of the vinyl magnesium halide to carry out reaction at a temperature of usually from −10 to 55° C., and preferably from 0 to 40° C., followed by hydrolysis using a dilute aqueous sulfuric acid, a saturated aqueous ammonium chloride or the like.

In the latter method, in which the 6,10-dimethyl-5-undecen-2-one is subjected to ethynylation and successive partial hydrogenation, the 6,10-dimethyl-5-undecen-2-one is first ethynylated by a conventional method to form 3,7,11-trimethyl-6-dodecen-1-yn-3-ol, having 15 carbon atoms and having a carbon-carbon triple bond at the terminal. Here, the ethynylation can be carried out by a known process as a process in which ketones are ethynylated to form compounds having a propargyl alcohol structure. When the ethynylation is carried out in a small scale, it is also possible to use a method with an acetylide of an alkali metal such as lithium, sodium or potassium or an alkaline earth metal such as calcium, or a method with an ethynyl magnesium halide.

When the ethynylation is carried out in an industrial scale, it is suitable to use, as described below, a method of direct ethynylation by acetylene in the presence of a strong base, because 3,7,11-trimethyl -6-dodecen-1-yn-3-ol can be produced at a low cost and the work up can be made easily. This direct ethynylation is carried out by a process in which the 6,10-dimethyl-5-undecen-2-one is allowed to react with acetylene, usually in an amount of from 1 to 10 moles per mole of the former, at −30° C. to 30° C. for 1 hour to 20 hours. The reaction is carried out under conditions where a strongly base compound containing an alkali metal such as sodium or potassium (e.g., a hydroxide of the alkali metal, an alkali metal alcoholate or an alkali metal amide) is present in a catalytic amount, and in an organic solvent which does not inhibit the reaction such as N,N-dimethylformamide, dimethyl sulfoxide, N-methylpyrrolidone, tetrahyrofuran, dimethyl ether, diethyl ether, methyl ethyl ether, anisole or dioxane, or liquid ammonia, or a mixed solvent of these. After the reaction, the acetylene is purged off from the reaction vessel, and 3,7,11-trimethyl-6-dodecen-1-yn-3-ol is obtained as a residue.

Next, the 3,7,11-trimethyl-6-dodecen-1-yn-3-ol obtained as described above is partially hydrogenated to give 3,7,11-trimethyl-1,6-dodecadien-3-ol. This partial hydrogenation intends to selectively reduce the carbon-carbon triple bond to a carbon-carbon double bond, and methods therefor are known per se. As methods for such reduction, a method in which a hydrogenating agent such as lithium aluminum hydride is used and a method in which a propargyl type alcohol is catalytically reduced in the presence of a hydrogenation catalyst in a solvent of a hydrocarbon such as n-hexane, n-heptane, octane, benzene, toluene or xylene, and/or an alcohol such as methanol, ethanol and propanol can be exemplified.

From an industrial viewpoint, the latter method is preferred. The hydrogenation of 3,7,11-trimethyl-6-dodecene-1-yn-3-ol is carried out, e.g., in an atmosphere of hydrogen, at a hydrogen pressure of from normal pressure to 50 kg/cm$^2$, and preferably from 2 to 20 kg/cm$^2$ and at a temperature of from 0 to 130° C., and preferably from 20 to 80° C. As the hydrogenation catalyst, a metal such as nickel, cobalt, palladium, platinum, rhodium or iridium or a compound containing any of these metals can be used. These can be supported on carriers such as activated carbon, barium sulfonate and calcium carbonate. In particular, in the present invention, a Lindlar catalyst comprising palladium sulfonate and calcium carbonate is especially preferable.

After the reaction is completed, 3,7,11-trimethyl -1,6-dodecadiene-3-ol can be isolated from the reaction mixture by a conventional method, e.g., by distillation.

Step (f):

In the step f, 6,10,14-trimethyl-5,9-pentadecadien -2-one is formed from the 3,7,11-trimethyl-1,6-dodecadien -3-ol obtained in the step (c). As a method for the step (f), either method is selected from a method in which the 3,7,11-trimethyl-1,6-dodecadien-3-ol is allowed to react with diketene or an acetoacetic acid ester to form an acetoacetic acid ester of 3,7,11-trimethyl-1,6-dodecadien-3-ol and subjecting the resultant ester to Carroll rearrangement, or a method in which the 3,7,11-trimethyl-1,6-dodecadien-3-ol is allowed to react with an isopropenyl alkyl ether to form an isopropenyl ether of 3,7,11-trimethyl-1,6-dodecadien-3-ol and subjecting the resultant ether to Claisen rearrangement.

This step (f) can be carried out following the procedure described in the step (d).

More specifically, in the former method, which employs Carroll rearrangement, first, the acetoacetic acid ester of 3,7,11-trimethyl-1,6-dodecadien-3-ol is formed by allowing 3,7,11-trimethyl-1,6-dodecadien-3-ol to react with diketene usually in an amount of from 0.8 to 2 moles, and preferably from 0.9 to 1.2 moles, per mole of the former. In this instance, the acetoacetic acid ester can be formed by merely making the 3,7,11-trimethyl-1,6-dodecadien-3-ol contact with diketene without a solvent or in an organic solvent which does not inhibit the reaction such as hydrocarbons or ethers. If necessary, the reaction can be conducted with heating to from 50 to 100° C. Also, an amine such as triethylamine or pyridine can be added in a catalytic amount to the reaction mixture, which accelerates the rate of esterification and improves the yield of the acetoacetic acid ester of 3,7,11-trimethyl-1,6-dodecadien-3-ol.

Next, the acetoacetic acid ester of 3,7,11-trimethyl-1,6-dodecadien-3-ol thus obtained is heated to usually from 130 to 180° C., and preferably from 150 to 180° C., in order to make the Carroll rearrangement (rearrangement and successive decarboxylation reaction) proceed to give 6,10,14-trimethyl-5,9-pentadecadien-2-one. At this step, an aluminum alkoxide such as aluminum isopropoxide can be added in a catalytic amount to the reaction mixture, which improves the yield of the 6,10,14-trimethyl-5,9-pentadecadien-2-one.

Also 6,10,14-trimethyl-5,9-pentadecadien-2-one can be obtained from the 3,7,11-trimethyl-1,6-dodecadien-3-ol and diketene in one pot by mixing the reactants necessary for the above two-step reaction (esterification reaction and Carroll rearrangement) all at once and controlling the reaction temperature.

In the foregoing, the reaction can be operated under similar conditions when an acetoacetic acid ester such as methyl acetoacetate or ethyl acetoacetate is used in place of the diketene, and the similar results as in the foregoing can be obtained.

Meanwhile, in the latter method, which employs Claisen rearrangement, the mixture of the 3,7,11-trimethyl-1,6-dodecadien-3-ol and an isopropenyl alkyl ether such as isopropeny methyl ether or isopropenyl ethyl ether in an amount of from 0.5 to 10 moles, and preferably from 0.8 to 3 moles, per mole of the former are heated at a temperature of from 50 to 200° C., and preferably from 100 to 200° C., in the presence of an acidic catalyst such as phosphoric acid, sulfuric acid, oxalic acid or trichloroacetic acid to effect isopropenyl etherification of the 3,7,11-trimethyl-1,6-dodecadien-3 -ol, and the resultant ether is converted into 6,10,14-trimethyl-5,9-pentadecadien-2-one by Claisen rearrangement.

After the reaction is completed, 6,10,14-trimethyl -5,9-pentadecadien-2-one can be isolated from the reaction mixture by a conventional method, e.g., by distillation.

Step (g):

In the step (g), the 6,10,14-trimethyl-5,9-pentadecadien-2-one obtained in the step (f) is subjected to hydrogenation to form phyton (6,10,14-trimethylpentadecan-2-one).

This step (g) can be carried out following the procedure described in the step (b).

More specifically, this hydrogenation can be carried out by a known method that can convert a carbon-carbon double bond to a saturated carbon-carbon bond. For example, the 6,10,14-trimethyl-5,9-pentadecadien-2-one can be hydrogenated generally in an autoclave, in the presence of a conventional hydrogenation catalyst comprised of palladium, platinum, Raney nickel, Raney cobalt or the like (preferably palladium on carbon), without solvent or in a solvent including hydrocarbons, alcohols, ethers, ketones, esters and carboxylic acids, under hydrogen pressure of from 1 to 100 kg/cm$^2$, and preferably from 1 to 20 kg/cm$^2$, and at a temperature of from 15 to 150° C., and preferably from 30 to 130° C. The reaction time can be appropriately set in accordance with the kind of the solvent or the hydrogen pressure.

After the reaction is completed, phyton (6,10,14-trimethylpentadecan-2-one) can be isolated from the reaction mixture by a conventional method, e.g., by distillation.

Step (h):

In the step (h), isophytol is formed from the phyton formed in the step (g). As a method for the step (h), either method is selected from a method in which the phyton is allowed to react with a vinyl magnesium halide to effect vinylation, or a method in which the phyton is subjected to ethynylation and successive partial hydrogenation.

This step (h) can be carried out following the procedure described in the step (c).

More specifically, in the former method, in which the phyton is allowed to react with a vinyl magnesium halide, isophytol (3,7,11,15-tetramethyl-1-hexadecen-3-ol) can be obtained by, e.g., adding the phyton to a vinyl magnesium halide prepared from a vinyl halide such as vinyl chloride or vinyl bromide and metal magnesium in a solvent such as tetrahydrofuran or diethyl ether, in such an amount of from 0.5 to 2 moles per mole of the vinyl magnesium halide to carry out reaction at a temperature of usually from −10 to 55° C., and preferably from 0 to 40° C., followed by hydrolysis using a dilute aqueous sulfuric acid, a saturated aqueous ammonium chloride or the like.

In the latter method, in which the phyton is subjected to ethynylation and successive partial hydrogenation, the phyton is first ethynylated by a conventional method to form 3,7,11,15-tetramethyl-1-hexadecyn-3-ol, having 20 carbon atoms and having a carbon-carbon triple bond at the terminal. Here, the ethynylation can be carried out by a known process process in which ketones are ethynylated to form compounds having a propargyl alcohol structure. When the ethynylation is carried out in a small scale, it is also possible to use a method with acetylide of an alkali metal such as lithium, sodium or potassium or an alkaline earth metal such as calcium, or a method with an ethynyl magnesium halide.

When the ethynylation is carried out in an industrial scale, it is suitable to use, as described below, a method of direct ethynylation by acetylene in the presence of a strong base, because 3,7,11,15-tetramethyl-1-hexadecyn-3-ol can be produced at a low production cost and the work up can be made easily. This direct ethynylation is carried out by a process in which the phyton is allowed to react with acetylene, usually in an amount of from 1 to 10 moles per mole of the former, at −30° C. to 30° C. for usually from 1 hour to 20 hours. The reaction is carried out under conditions where a strong base containing an alkali metal such as sodium or potassium (e.g., a hydroxide of the alkali metal, an alkali metal alcoholate or an alkali metal amide) is present in a catalytic amount, and in an organic solvent which does not inhibit the reaction such as N,N-dimethylformamide, dimethyl sulfoxide, N-methylpyrrolidone, tetrahyrofuran, dimethyl ether, diethyl ether, methyl ethyl ether, anisole or dioxane, or liquid ammonia, or a mixed solvent of these. After the reaction, the acetylene is purged off from the reaction vessel, and 3,7,11,15-tetramethyl-1-hexadecyn-3-ol is obtained as a residue.

Next, the 3,7,11,15-tetramethyl-1-hexadecyn-3-ol thus obtained is partially hydrogenated to give the isophytol. This partial hydrogenation intends to selectively reduce the carbon-carbon triple bond to a carbon-carbon double bond, and methods therefor are known per se. As methods for such reduction, a method in which a hydrogenating agent such as lithium aluminum hydride is used and a method in which a propargyl type alcohol is catalytically reduced in the presence of a hydrogenation catalyst in a solvent of a hydrocarbon such as n-hexane, n-heptane, octane, benzene, toluene or xylene, and/or an alcohol such as methanol, ethanol or propanol can be exemplified.

From an industrial viewpoint, the latter method is preferred. The hydrogenation of 3,7,11,15-tetramethyl-1-hexadecyn-3-ol is carried out, e.g., in an atmosphere of hydrogen, at a hydrogen pressure of from normal pressure to 50 kg/cm$^2$, and preferably from 2 to 20 kg/cm$^2$, and at a temperature of from 0 to 130° C., and preferably from 20 to 80° C. As the hydrogenation catalyst, a metal such as nickel, cobalt, palladium, platinum, rhodium or iridium or a compound containing any of these metals can be used. These can be supported on carriers such as activated carbon, barium sulfonate and calcium carbonate. In particular, in the present invention, a Lindlar catalyst comprising palladium supported on calcium carbonate is especially preferable.

After the reaction is completed, isophytol can be isolated from the reaction mixture by a conventional method, e.g., by distillation.

Further, the production process according to the third embodiment of the present invention that achieves the third object of the present invention will be described below.

The production process according to the third embodiment of the present invention is a process for producing a 6-methyl-2-heptanone analogue represented by Formula (1):

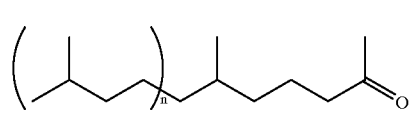

(1)

wherein n is an integer of 0 or 1 or more;

the process comprising the step of allowing hydrogen, acetone and an aldehyde represented by Formula (2):

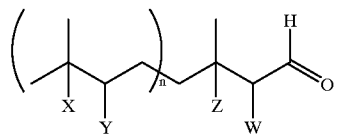

(2)

wherein n is as defined above; X and Y each represents hydrogen atom or they are coupled together to form a carbon-carbon bond; and Z and W each represents a hydrogen atom or they are coupled together to form a carbon-carbon bond;

to react in the presence of an aqueous alkali solution containing an alkaline substance, and a hydrogenation catalyst. In this process, in order to improve the yield of the 6-methyl-2-heptanone analogue of Formula (1), it is preferable to make the aldehyde of Formula (2) and the aqueous alkali contact with hydrogen while each continuously adding the aldehyde compound and the aqueous alkali to a suspension of the hydrogenation catalyst in the acetone.

In the third embodiment of the present invention, there are no particular limitations on the ratio of the acetone to the aldehyde of Formula (2). However, in order to improve the selectivity to the 6-methyl-2-heptanone analogue of Formula (1) on the basis of the aldehyde of Formula (2), which is more expensive, acetone is preferably used within the range of from 0.5 mole to 10 moles per mole of the aldehyde of Formula (2). From the viewpoint of improving the volumetric efficiency of the reaction to reduce the amount of unreacted acetone which should be recovered, the acetone is more preferably used within the range of from 0.8 mole to 5 moles, and particularly preferably from 0.9 mole to 3 moles, per mole of the aldehyde of Formula (2).

The alkaline substance used in the third embodiment of the present invention includes, e.g., alkali metal hydroxides such as sodium hydroxide and potassium hydroxide, alkaline-earth metal hydroxides such as barium hydroxide and calcium hydroxide, alkali metal carbonates such as potassium carbonate, and amine compounds such as piperidine. In particular, alkali metal hydroxides and alkaline-earth metal hydroxides are preferred as the alkaline substance. The alkaline substance can be used alone or in combination of two or more types.

The alkaline substance can be used in an amount of usually from 0.001 to 0.2 mole per mole of the aldehyde of Formula (2), and, from the viewpoint of reaction rate and production cost of the 6-methyl-2-heptanone analogue of Formula (1), preferably from 0.01 to 0.1 mole per mole of the aldehyde of Formula (2).

The alkaline substance can be used in the aqueous alkali in a concentration of usually from 0.5 to 30% by weight/, and preferably from 1 to 10% by weight.

As the hydrogenation catalyst in the third embodiment of the present invention, catalysts conventionally used when carbon-carbon double bonds of unsaturated carbonyl compounds are selectively hydrogenated can be employed, including, e.g., catalysts comprising palladium, rhodium, nickel, platinum or the like as an active component.

The hydrogenation catalyst includes a metal itself, a metal oxide, an alloy of the several kinds of metals, and ones with an active component supported on carriers such as activated carbon, alumina, silica gel and kieselguhr. Among them, palladium on carbon, palladium on alumina, Raney nickel and platinum on carbon are preferred. Further, palladium on carbon and palladium on alumina are more preferred.

The hydrogenation catalyst is usually used in an amount of from 0.01 to 10% by weight based on the weight of the aldehyde of Formula (2). From the viewpoints of reaction rate and the production cost of the 6-methyl-2-heptanone analogue of Formula (1), the hydrogenation catalyst is preferably used in an amount of from 0.03 to 3% by weight based on the weight of the aldehyde of Formula (2).

In the third embodiment of the present invention, it is not always necessary to use a solvent. However, so long as the progress of reaction is not inhibited, an appropriate solvent can be used. Usable solvents include, e.g., aliphatic alcohols such as methanol, ethanol, propanol, isopropanol, n-butanol, s-butanol and t-butanol; ethers such as tetrahydrofuran, 1,4-dioxane, diethyl ether, diisopropyl ether and di-n-butyl ether; and hydrocarbons such as hexane, heptane, octane, benzene, toluene and xylene.

As a specific operation for the production process of the third embodiment of the present invention, the aldehyde of Formula (2), acetone, an aqueous alkali and a hydrogenation catalyst are mixed together at a temperature within a predetermined range and in an atmosphere of hydrogen, in a usual manner of operation, without requiring any special equipment.

In such operation, there are no particular limitations on the order or the rate of the addition of the respective components. All the components, i.e., acetone, an aldehyde of Formula (2), an aqueous alkali and a hydrogenation catalyst can be mixed at one time. In addition one or two of acetone, an aldehyde of Formula (2) and an aqueous alkali can be introduced into a reaction vessel together with the hydrogenation catalyst and the remaining components is continuously added to the reaction vessel. Here, the term "continuously add" embraces an embodiment that the said remaining components are added in parts by several times.

In particular, as a method of mixing the respective components, in order to prevent the runaway of the reaction and to produce the 6-methyl-2-heptanone analogue of Formula (1) in a high yield and selectivity, a method is preferred in which an aqueous alkali and an aldehyde of Formula (2) are each continuously added to a suspension of a hydrogenation catalyst in acetone. In this case, acetone can be present in great excess to the aldehyde of Formula (2) in the reaction mixture during the greater period of the reaction, so that side reactions due to, e.g., self condensation of the aldehyde of Formula (2) are supressed and the corresponding 6-methyl-2-heptanone analogue of Formula (1) can be obtained in a high yield and selectivity.

The reaction is usually carried out at a temperature ranging from 20 to 180° C., and preferably from 40 to 140° C., in order to control the reaction rate at a practical level and also to improve the selectivity to the 6-methyl-2-heptanone analogue of Formula (1).

The time for the reaction depends on the kind and concentration of the alkaline substance and on the reaction temperature. In the case when, as previously stated, the aqueous alkali and the aldehyde of Formula (2) are each continuously added to the suspension of the hydrogenation catalyst in acetone, the aldehyde of Formula (2) and the aqueous alkali may be added for 30 minutes to 10 hours. After their addition is completed, the reaction can further be run to the completion for 0 to 10 hours.

In the course the aldehyde of Formula (2) and the aqueous alkali are added and in the course the reaction is run to the completion, the reaction mixture is preferably stirred thoroughly.

In the third embodiment of the present invention, the hydrogen is made to contact with the surface of a mixture of acetone, an aldehyde of Formula (2), an aqueous alkali and a hydrogenation catalyst. Also hydrogen can be introduced (bubbled) into the mixture.

The pressure of hydrogen is usually within the range of from 1 to 100 atmospheric pressure. A pressure within the range of from 1 to 10 atmospheric pressure is preferable because a usual reaction vessel can be used.

After the reaction is completed, the 6-methyl-2-heptanone analogue of Formula (1) can be isolated by a usual method, e.g., a method in which the hydrogenation catalyst is removed from the reaction mixture by filtration, centrifugal separation or the like method, followed by separation of the aqueous layer, and the resulting organic layer is distilled, or a method in which the hydrogenation catalyst is removed from the reaction mixture, followed by extraction with an organic solvent, and the resulting organic layer is concentrated under normal pressure or reduced pressure. The organic solvent used in the above extraction includes, e.g., hydrocarbons such as toluene, benzene, hexane and cyclohexane, and halogenated hydrocarbons such as methylene chloride, chloroform, carbon tetrachloride and dichloroethane.

As described above, according to the third embodiment of the present invention, industrially readily available materials (the aldehyde of Formula (2), e.g., isovaleraldehyde, and acetone) are contact with hydrogen in the presence of an aqueous alkali and a hydrogenation catalyst, to give the corresponding 6-methyl-2-heptanone analogue of Formula (1) in one pot, in a high yield and selectivity on the basis of the aldehyde compound of Formula (2).

In the aldehyde of Formula (2), n is an integer of 0 or 1 or more. In particular, aldehydes wherein n is 0, 1 or 2 are preferred. In such a case, the integer n in the 6-methyl-2-heptanone analogue of Formula (1) is 0, 1 or 2 corresponding to the integer n of the aldehyde of Formula (2).

Here, as examples of the aldehyde of Formula (2) wherein n is 0, they include senecioaldehyde (Z and W are coupled together to form a carbon-carbon bond) and isovaleraldehyde (Z and W represent both hydrogen atoms). In this case, as the compound of Formula (1), 6-methyl-2-heptanone (n is 0) is obtained.

As examples of the aldehyde of Formula (2) wherein n is 1, they include citral (X and Y are coupled together to form a carbon-carbon bond and Z and W are coupled together to form a carbon-carbon bond), citronellal (X and Y are coupled together to form a carbon-carbon bond and Z and W are both hydrogen atoms) and tetrahydrocitral (X and Y, and Z and W are all hydrogen atoms). In this case, as the compound of Formula (1), 6,10-dimethyl-2-undecanone (n is 1) is obtained.

As examples of the aldehyde of Formula (2) wherein n is 2, they include farnesal (X and Y are coupled together to form a carbon-carbon bond and Z and W are coupled together to form a carbon-carbon bond) and hexahydrofarnesal (X and Y, and Z and W are all hydrogen atoms). In this case, as the compound of Formula (1), phyton (n is 2) is obtained.

As examples of the aldehyde of Formula (2) wherein n is 3, they include 3,7,11,15-tetramethyl-2,6,10,14-hexadecatetraenal (X and Y are coupled together to form a carbon-carbon bond and Z and W are coupled together to form a carbon-carbon bond), 3,7,11,15-tetramethyl -6,10,14-hexadecatrienal (X and Y are coupled together to form a carbon-carbon bond and Z and W are both hydrogen atoms) and 3,7,11,15-tetramethylhexadecanal (X and Y, and Z and W are all hydrogen atoms). In this case, as the compound of Formula (1), 6,10,14,18-tetramethyl-2-nonadecanone (n is 3) is obtained.

As examples of the aldehyde of Formula (2) wherein n is 4, they include 3,7,11,15,19-pentamethyl-2,6,10,14,18-eicosapentaenal (X and Y are coupled together to form a carbon-carbon bond and Z and W are coupled together to form a carbon-carbon bond), 3,7,11,15,19-pentamethyl-6,10,14,18-eicosatetraenal (X and Y are coupled together to form a carbon-carbon bond and Z and W are both hydrogen atoms) and 3,7,11,15,18-pentamethyleicosanal (n is 4, X and Y, and Z and W are all hydrogen atoms). In this case, as the compound of Formula (1), 6,10,14,18,22-pentamethyl-2-tricosanone (n is 4) is obtained.

In the third embodiment of the present invention, the aldehyde of Formula (2) can be used alone, or can be used in the form of a mixture of two or more types having the same number of carbon atoms.

Phyton or isophytol can be produced using, as a material, the 6-methyl-2-heptanone analogue of Formula (1) thus obtained (n is 0, 1 or 2).

For example, from the 6-methyl-2-heptanone, i.e., the compound of Formula (1) wherein n is 0, phyton can be obtained by subjecting the 6-methyl-2-heptanone to the steps (c) to (g) described in the second embodiment of the present invention, and isophytol can be obtained by further subjecting the above phyton to the step (h) described in the second embodiment of the present invention. From the phyton, i.e., the compound of Formula (1) wherein n is 2, isophytol can be obtained by subjecting the phyton to the step (h) described in the second embodiment of the present invention. Further, from the 6,10-dimethyl-2-undecanone, i.e., the compound of Formula (1) wherein n is 1, phyton can be obtained by subjecting the 6,10-dimethylundecan-2-one to steps (e') to (g') described below, and isophytol can be obtained by further subjecting the above phyton to the step (h) described in the second embodiment of the present invention.

Step (e'):

A step where 3,7,11-trimethyl-1-dodecen-3-ol is formed from the 6,10-dimethyl-2-undecanone by adding a vinyl group to the carbonyl group at its terminal. As a method for the step (e'), either method is selected from a method in which the 6,10-dimethyl-2-undecanone is allowed to react with a vinyl magnesium halide to effect vinylation, or a method in which the 6,10-dimethyl-2-undecanone is subjected to ethynylation and successive partial hydrogenation.

For the industrial application, it is more advantageous to effect the latter ethynylation and successive partial hydrogenation.

This step (e') can be carried out following the procedure described in the step (c) in the second embodiment of the present invention.

More specifically, in the former method, in which the 6,10-dimethyl-2-undecanone is allowed to react with a vinyl magnesium halide reagent, the 3,7,11-trimethyl-1-dodecen-3-ol can be obtained by, e.g., adding the 6,10 -dimethyl-2-undecanone to a vinyl magnesium halide prepared from a vinyl halide such as vinyl chloride or vinyl bromide and metal magnesium in a solvent such as tetrahydrofuran or diethyl ether, in such an amount of from 0.5 to 2 moles per mole of the vinyl magnesium halide to carry out reaction at a temperature of usually from −10 to 55° C., and preferably from 0 to 40° C., followed by hydrolysis using a dilute aqueous sulfuric acid, a saturated aqueous ammonium chloride or the like.

In the latter method, in which the 6,10-dimethyl-2-undecanone is subjected to ethynylation and successive partial hydrogenation, the 6,10-dimethyl-2-undecanone is first ethynylated by a conventional method to form 3,7,11-trimethyldodecan-1-yn-3-ol, having 15 carbon atoms and having a carbon-carbon triple bond at the terminal. Here, the ethynylation can be carried out by a known process as a process in which ketones are ethynylated to form compounds having a propargyl alcohol structure. When the ethynylation is carried out in a small scale, it is also possible to use a method with an acetylide of an alkali metal such as lithium, sodium or potassium or an alkaline earth metal such as calcium or a method with an ethynyl magnesium halide.

When the ethynylation is carried out in an industrial scale, it is suitable to use, as described below, a method of direct ethynylation by acetylene in the presence of a strong base catalyst, because 3,7,11-trimethyldodecan-1-yn-3-ol can be produced at a low production cost and the work up can be made easily. This direct ethynylation is carried out by a process in which the 6,10-dimethyl-2-undecanone is allowed to react with acetylene, usually in an amount of from 1 to 10 moles per mole of the former, at −30° C. to 30° C. for 1 hour to 20 hours. The reaction is carried out under conditions where a strong base compound containing an alkali metal such as sodium or potassium (e.g., a hydroxide of the alkali metal, an alkali metal alcoholate or an alkali metal amide) is present in a catalytic amount, and in an organic solvent which does not inhibit the reaction such as N,N-dimethylformamide, dimethyl sulfoxide, N-methylpyrrolidone, tetrahyrofuran, dimethyl ether, diethyl ether, methyl ethyl ether, anisole or dioxane, or liquid ammonia, or a mixed solvent of these. After the reaction, the acetylene is purged off from the reaction vessel, and 3,7,11-trimethyldodecan-1-yn-3-ol is obtained as a residue.

Next, the 3,7,11-trimethyldodecan-1-yn-3-ol obtained as described above is partially hydrogenated to give the 3,7,11-trimethyl-1-dodecen-3-ol. This partial hydrogenation intends to selectively reduce the carbon-carbon triple bond to a carbon-carbon double bond, and methods therefor are known per se. As methods for such reduction, a method in which a hydrogenating agent such as lithium aluminum hydride is used and a method in which a propargyl type alcohol is catalytically reduced in the presence of a hydrogenation catalyst in a solvent of a hydrocarbon such as n-hexane, n-heptane, octane, benzene, toluene or xylene, and/or an alcohol such as methanol, ethanol and propanol can be exemplified.

From an industrial viewpoint, the latter method is preferred. The hydrogenation of 3,7,11-trimethyldodecan-1-yn-3-ol is carried out, e.g., in an atmosphere of hydrogen, at a hydrogen pressure of from normal pressure to 50 kg/cm$^2$, and preferably from 2 to 20 kg/cm$^2$, and at a temperature of from 0 to 130° C., and preferably from 20 to 80° C. As the hydrogenation catalyst, a metal such as nickel, cobalt, palladium, platinum, rhodium or iridium or a compound containing any of these metals can be used. These can be supported on carriers such as activated carbon, barium sulfonate and calcium carbonate. In particular, in the present invention, a Lindlar catalyst comprising palladium supported on calcium carbonate is especially preferable.

After the reaction is completed, 3,7,11-trimethyl-1-dodecan-3-ol can be isolated from the reaction mixture by a conventional method, e.g., by distillation.

Step (f'):

A step where 6,10,14-trimethyl-5-pentadecen-2-one is formed from the 3,7,11-trimethyl-1-dodecen-3-ol obtained in the step (e'). As a method for the step (f)', either method is selected from a method in which the 3,7,11-trimethyl-1- dodecen-3-ol is allowed to react with diketene or an acetoacetic acid ester to form an acetoacetic acid ester of 3,7,11-trimethyl-1-dodecen-3-ol and subjecting the resultant ester to Carroll rearrangement, or a method in which the 3,7,11-trimethyl-1-dodecen-3-ol is allowed to react with an isopropenyl alkyl ether to form an isopropenyl ether of 3,7,11-trimethyl-1-dodecen-3-ol and subjecting the resultant ether to Claisen rearrangement.

This step (f') can be carried out following the procedure described in the step (d) in the second embodiment of the present invention.

More specifically, in the former method, which employs Carroll rearrangement, first, the acetoacetic acid ester of 3,7,11-trimethyl-1-dodecen-3-ol is formed by allowing 3,7,11-trimethyl-1-dodecen-3-ol to react with diketene usually in an amount of from 0.8 to 2 moles, and preferably from 0.9 to 1.2 moles, per mole of the former. In this instance, the acetoacetic acid ester can be formed by merely making the 3,7,11-trimethyl-1-dodecen-3-ol contact with the diketene without a solvent or in an organic solvent which does not inhibit to the reaction such as hydrocarbons or ethers. If necessary, the reaction can be conducted with heating to from 50 to 100° C. Also, an amine such as triethylamine or pyridine can be added in a catalytic amount to the reaction mixture, which accelerates the rate of esterification and improves in the yield of the acetoacetic acid ester of 3,7,11-trimethyl-1-dodecen-3-ol.

Next, the acetoacetic acid ester of 3,7,11-trimethyl-1-dodecen-3-ol thus obtained is heated to usually from 130 to 180° C., and preferably from 150 to 180° C., in order to make the Carroll rearrangement (rearrangement and successive decarboxylation) proceed to give 6,10,14-trimethyl-5-pentadecen-2-one. At this step, an aluminum alkoxide such as aluminum isopropoxide can be added in a catalytic amount to the reaction mixture, which improves the yield of the 6,10,14-trimethyl-5-pentadecen-2-one.

Also, the 6,10,14-trimethyl-5-pentadecen-2-one can be obtained from the 3,7,11-trimethyl-1-dodecen-3-ol and diketene in one pot by mixing the reactants necessary for the above two-step reaction (esterification and Carroll rearrangement) all at once and controlling the reaction temperature.

In the foregoing, the reaction can be operated under similar conditions when an acetoacetic acid ester such as methyl acetoacetate or ethyl acetoacetate is used in place of diketene, and the similar results as in the foregoing can be obtained.

Meanwhile, in the latter method, which employs Claisen rearrangement, the mixture of 3,7,11-trimethyl-1-dodecen-3-ol and an isopropenyl ether such as isopropenyl methyl ether of isopropenyl ethyl ether in an amount of from 0.5 to 10 moles, and preferably from 0.8 to 3 moles, per mole of the former are heated at a temperature of from 50 to 200° C., and preferably from 100 to 200° C., in the presence of an acidic catalyst such as phosphoric acid, sulfuric acid, oxalic acid or trichloroacetic acid to effect isopropenyl etherification of the 3,7,11-trimethyl-1-dodecen-3-ol, and the resultant ether is converted into 6,10,14-trimethyl-5-pentadecen-2-one by Claisen rearrangement.

After the reaction is completed, 6,10,14-trimethyl-5-pentadecen-2-one can be isolated from the reaction mixture by a conventional method, e.g., by distillation.

Step (g'):

The 6,10,14-trimethyl-5-pentadecen-2-one obtained in the step (f') is subjected to hydrogenation to form phyton (6,10,14-trimethylpentadecan-2-one).

This step (g') can be carried out following the procedure described in the step (b) in the second embodiment of the present invention.

More specifically, this hydrogenation can be carried out by a known method that can convert a carbon-carbon double bond to a saturated carbon-carbon bond. For example, the 6,10,14-trimethyl-5-pentadecen-2-one can be hydrogenated generally in an autoclave, in the presence of a conventional hydrogenation catalyst comprised of palladium, platinum, Raney nickel, Raney cobalt or the like (preferably palladium on carbon), without solvent or in a solvent including hydrocarbons, alcohols, ethers, ketones, esters and carboxylic acids, under hydrogen pressure of from 1 to 100 kg/cm$^2$, and preferably from 1 to 20 kg/cm$^2$, and at a temperature of from 15 to 150° C. and preferably from 30 to 130° C. The reaction time can be appropriately set in accordance with the kind of the solvent or and the hydrogen pressure.

After the reaction is completed, phyton (6,10,14-trimethylpentadecan-2-one) can be isolated from the reaction mixture by a conventional method, e.g., by distillation.

EXAMPLES

The present invention will be described below in detail. The present invention is by no means limited to these Examples.

Example 1

An autoclave made of stainless steel, equipped with a stirrer and a jacket and having an internal volume of 10 liters, was charged with 1,403.1 g (24.2 moles) of acetone in an atmosphere of nitrogen, and then heated with stirring at the jacket temperature of 72° C. At the time the temperature and pressure inside the autoclave reached 68° C. and 1.9 kg/cm$^2$ (gauge pressure), respectively, aqueous 2% sodium hydroxide and isovaleraldehyde were each continuously fed, the former at a rate of 774 g/hr and the latter at 679 g/hr. After they were began to be fed, the temperature inside the autoclave gradually became higher. The feed of aqueous 2% sodium hydroxide and isovaleraldehyde were continued for 175 minutes while keeping the temperature inside the autoclave at 70 to 72° C. with stirring. The amount of aqueous 2% sodium hydroxide fed during this time was 2,253.7 g (1.12 moles in terms of NaOH), and the amount of isovaleraldehyde fed was 1,979.4 g (22.99 moles).

After the feed of the aqueous 2% sodium hydroxide and isovaleraldehyde was completed, the reaction mixture was kept at temperatures within the above range and stirred for 1.5 hours to run the reaction to the completion. After cooling to room temperature, the reaction mixture was taken out and left to stand, then separated into two layers. The organic layer (upper layer) was collected, and analyzed by gas chromatography (column: DC QF1, available from Gaskuro Kogyou Inc.; Column length: 1 m; Column temperature: raised from 60° C. to 200° C.; Rising Rate of temperature: 5° C./min.) to find that 1,909.0 g (yield: 66%) of 6-methyl-3-hepten-2-one and 107.3 g (yield: 3.3%) of 6-methyl-4-hydroxyheptan-2-one were contained in 2,938.8 g of the organic layer. The conversion of isovaleraldehyde was 98.3%.

2,938.8 g of the organic layer thus obtained was distilled under reduced pressure to give 1,824.3 g (purity: 98%) of 6-methyl-3-hepten-2-one (b.p.: 113–115° C./100 mmHg).

Example 2

An autoclave made of stainless steel, equipped with a stirrer and a jacket and having an internal volume of 10 liters, was charged with 1,470 g (25.3 moles) of acetone and 217 g (2.52 moles) of isocaleraldehyde in an atmosphere of nitrogen, and the resultant mixture was heated with stirring at the jacket temperature of 60° C. At the time the temperature and pressure inside the autoclave reached 57.7° C. and 1.0 kg/cm² (gauge pressure), respectively, aqueous 2% sodium hydroxide and isovaleraldehyde were each continuously fed into the above mixture, the former at a rate of 774 g/hr and the latter at 605 g/hr. About 3 minutes after the feed of them had been started, the temperature inside the autoclave began to rise, and, 5 minutes thereafter, it reached a maximum temperature of 70.6° C. About 4 minutes after the temperature inside the autoclave began to rise, the pressure inside the autoclave reached a maximum pressure of 1.8 kg/cm².

10 minutes after the feed of the aqueous 2% sodium hydroxide and isovaleraldehyde had been started, the jacket temperature was set at 70 to 72° C. and the reaction was continued while keeping the temperature inside the autoclave at 63.4 to 71.2° C. The feed of the aqueous 2% sodium hydroxide and isovaleraldehyde was continued for 175 minutes until 2,256.2 g (1.128 moles in terms of Sodium hydroxide) of the aqueous 2% sodium hydroxide and 1,764.1 g (20.51 moles) of the isovaleraldehyde were added in the acetone.

After the feed of the aqueous 2% sodium hydroxide and isovaleraldehyde was completed, the resultant reaction mixture was stirred for 1.5 hours at the same temperatures to run the reaction to the completion. After cooling to room temperature, the reaction mixture was taken out and left to stand, then separated into two layers. The organic layer (upper layer) was collected, and analyzed by gas chromatography to find that 1,926.1 g (yield: 66.5%) of 6-methyl-3-hepten-2-one and 107.4 g (yield: 3.3%) of 6-methyl-4-hydroxyheptan-2-one were contained in 2,993.8 g of the organic layer. The conversion of isovaleraldehyde was 98.2%.

Comparative Example 1

An example is shown below in which the reaction vessel equipped with a stirrer and a reflux condenser was charged with acetone, isovaleraldehyde and aqueous 2% sodium hydroxide at the same time.

More specifically, the inside of a reaction vessel having an internal volume of 300 ml was thoroughly replaced with nitrogen, and then 30.5 g (525 mmols) of acetone, 43.1 g (500 mmols) of isovaleraldehyde and 50.0 g (50 mmols in terms of NaOH) of aqueous 2% sodium hydroxide were added at the same time into the reaction vessel, followed by stirring at the temperature inside the reaction vessel of of 45° C. The heat generated with the reaction raised the temperature inside the reaction vessel up to 55° C. The resultant reaction mixture was stirred at the temperatures inside the reaction vessel of 55 to 65° C.

After cooling to room temperature, the reaction mixture was taken out and made to separate into two layers. The organic layer (upper layer) was collected and analyzed by gas chromatography to find that 35.7 g (yield: 56.6%) of 6-methyl-3-hepten-2-one was contained in 64.3 g of the organic layer.

As is seen from this result, when the acetone, isovaleraldehyde and aqueous 2% sodium hydroxide are added at the same time into the reaction vessel, the yield of the 6-methyl-3-hepten-2-one is reduced.

Example 3

(Step (a))

The procedure of Example 1 was repeated using 1,470.0 g (25.3 moles) of acetone, 1,981.9 g (23.0 moles) of isovaleraldehyde and 2,256.2 (1.128 moles in terms of NaOH) of aqueous 2% sodium hydroxide, to give 2,993.8 g of an organic layer containing 1,926.1 g (yield: 66.5%) of 6-methyl-3-hepten-2-one.

(Step (b))

An autoclave having an internal volume of 5 liters was charged with 2,823.3 g of the organic layer containing 1,816.4 g (14.4 moles) of 6-methyl-3-hepten-2-one, obtained by the above step (a), and 1.93 g of a 5% palladium on carbon catalyst to carry out the hydrogenation for 7 hours under hydrogen pressure of 5 to 9 kg/cm² at a reaction temperature of 120° C.

Thereafter, the catalyst was filtered off, and the resultant filtrate was analyzed by gas chromatography (capillary column: CBP-10, available from Gasukuro Kogyo Inc.; column length: 50 m; column temperature: raised from 70 to 240° C.; rising rate of temperature: 5° C./min.) to find that 1,890.4 g (yield: 100%) of 6-methyl-2-heptanone was contained in the filtrate.

Next, the acetone was removed from this filtrate under normal pressure, then components having boiling points of 33 to 132° C. were removed under a pressure of 300 mmHg. The residue was purified with distillation to give 1,628.9 g of 6-methyl-2-heptanone (boiling point: 103° C./100 mmHg; purity: 99% or higher).

(Step (c))

An autoclave having an internal volume of 3 liters was charged with 31.0 g (221.4 mmols in terms of KOH) of aqueous 40% potassium hydroxide, 1.1 kg (64.7 moles) of liquid ammonia and 0.18 kg (6.92 moles) of acetylene. Thereafter, keeping the temperature inside the autoclave at 4 to 6° C., 435.9 g (3.366 moles) of the 6-methyl-2-heptanone obtained in the step (b) was introduced into the autoclave to initiate the ethynylation.

The ethynylation was carried out at 4 to 6° C. for 2 hours, and then 69.8 g of aqueous 25% ammonium sulfate was introduced into the autoclave to stop the reaction. Thereafter, ammonia was purged off from the autoclave while gradually raising the temperature inside the autoclave to room temperature.

Next, 220 g of hexane and 440 g of water were added to the autoclave. A hexane solution containing 3,7-dimethyl-1-octyn-3-ol was obtained by collecting the organic layer, followed by washing with water. Above the procedures for the ethynylation of 6-methyl-2-heptanone were repeated twice (three times in total) to obtain, in total, 2,280 g of a hexane solution containing 3,7-dimethyl-1-octyn-3-ol (hexane content: 680 g). The conversions of 6-methyl-2-heptanone were, as a result of analysis by gas chromatography (column: PEG-20M, available from Gasukuro Kogyo Inc.; column length: 3 m; column temperature: 140° C.), 94.7%, 98.0% and 97.2% for the respective runs of the ethynylation.

An autoclave having an internal volume of 3 liters was charged with 1,140 g of the hexane solution containing 3,7-dimethyl-1-octyn-3-ol thus obtained and 0.27 g of a Lindlar catalyst (supported on calcium carbonate) to carry out the hydrogenation for 4 hours under hydrogen pressure of 5 to 8 kg/cm² (gauge pressure) at a temperature of 25 to 43° C. Thereafter, the catalyst was filtered off, and the resultant filtrate was concentrated with a rotary evaporator to give crude 3,7-dimethyl-1-octen-3-ol. Above the procedures for the hydrogenation of 3,7-dimethyl-1-octyn-3-ol were repeated once more to obtain, in total, 1,590 g of crude 3,7-dimethyl-1-octen-3-ol. Analysis by gas chromatography (column: DC-550, available from Gasukuro Kogyo Inc.;

column length: 3 m; column temperature: 100° C.; and column: PEG-HT, available from Gasukuro Kogyo Inc.; column length: 3 m; column temperature: 130° C.) revealed that the conversions of 3,7-dimethyl-1-octyn-3-ol were 99.7% and 97.3% for the respective runs of the hydrogenation, and the selectivities to 3,7-dimethyl-1-octen-3-ol were 95.0% and 95.8%, respectively.

To 1,590 g of the crude 3,7-dimethyl-1-octen-3-ol thus obtained, 0.41 g of a methanolic sodium methoxide (concentration: 28%) was added, then the resulting mixture was heated at 150° C. for 1 hour to decompose unreacted 3,7-dimethyl-1-octyn-3-ol. Thereafter, the resultant solution was simple distilled under a pressure of about 50 mmHg to collect 1,440 g of a fraction having a boiling point of about 115° C. This fraction was purified by removing low-boiling components (boiling point: about 80° C./about 20 mmHg) while heating under reduced pressure, to give 1,360 g of a residue. Analysis by gas chromatography (column: DC-550, available from Gasukuro Kogyo Inc.; column length: 3 m; column temperature: raised from 120 to 190° C.; rising rate of temperature rise: 5° C./min.) revealed that this residue contained 93.1% of 3,7-dimethyl-1-octen-3-ol (yield on the basis of 6-methyl-2-heptanone: 80.2%).

(Step (d))

A three-necked flask made of glass, equipped with a reflux condenser and having an internal volume of 2 liters was charged with 680 g (4.05 moles) of the 3,7-dimethyl-1-octen-3-ol obtained in the step (c), 2.23 g (22 mmols) of triethylamine and 5.21 g (26 mmols) of aluminum isopropoxide. To the resulting mixture, 328 g (3.905 moles) of diketene was added dropwise over a period of 1.5 hours while heating at 70 to 80° C., and the reaction was carried out for further 1 hour. Thereafter, the temperature of the reaction mixture was raised to 170° C. to carry out the reaction for further 3 hours. The above procedures for the hydrogenation of 3,7-dimethyl-1-octen-3-ol with diketene were repeated once more to obtain, in total, 1,650 g of a reaction mixture (crude 6,10-dimethyl-5-undecen-2-one). Analysis by gas chromatography (column: DC-550, available from Gasukuro Kogyo Inc.; column length: 3 m; column temperature: raised from 120 to 190° C.; rising rate of temperature: 5° C./min.) revealed that the conversions of 3,7-dimethyl-1-octen-3-ol were 93.1% and 92.7% for the respective runs of the reaction.

Under a pressure of 7 mmHg, 1650 g of the reaction mixture (crude 6,10-dimethyl-5-undecen-2-one) thus obtained was simple distilled to collect 1,350 g of a fraction having a boiling point of 85 to 110+ C. The fraction obtained was purified by distillation to give 1,100 g of 6,10-dimethyl-5-undecen-2-one (boiling point: about 120° C./6 mmHg, purity: 99.4% (yield: 69.2%)).

(Step (e))

An autoclave having an internal volume of 3 liters was charged with 23.6 g (169 mmols in terms of KOH) of aqueous 40% potassium hydroxide, 1.0 kg (58.8 moles) of liquid ammonia and 0.18 kg (6.92 moles) of acetylene. Thereafter, keeping the temperature inside the autoclave at 4 to 6° C., 550.0 g (2.784 moles) of the 6,10-dimethyl-5-undecen-2-one obtained in the step (d) was introduced into the autoclave to initiate the ethynylation.

The ethynylation was carried out at 4 to 6° C. for 1.75 hours, and then 53.3 g of aqueous 25% ammonium sulfate was introduced into the autoclave to stop the reaction. Thereafter, ammonia was purged off from the autoclave while gradually raising the temperature inside the autoclave to room temperature.

Next, 280 g of hexane and 550 g of water were added to the autoclave. A hexane solution containing 3,7,11-trimethyl-6-dodecen-1-yn-3-ol was obtained by collecting the organic layer, followed by washing with water. From this hexane solution, the hexane was removed with a rotary evaporator to give 630 g of crude 3,7,11-trimethyl-6-dodecen-1-yn-3-ol. Analysis by gas chromatography (column: PEG-20M, available from Gasukuro Kogyo Inc.; column length: 3 m; column temperature: 190° C.) revealed that the conversion of 6,10-dimethyl-5-undecen-2-one was 98.0%.

An autoclave having an internal volume of 3 liters was charged with 630 g of the 3,7,11-trimethyl-6-dodecen-1-yn-3-ol thus obtained, 270 g of hexane and 0.22 g of a Lindlar catalyst (supported on calcium carbonate) to carry out the hydrogenation for 4 hours under hydrogen pressure of 5 to 8 kg/cm² (gauge pressure) at a temperature of 25 to 43° C. Thereafter, the catalyst was filtered off, and the resultant filtrate was concentrated with a rotary evaporator to give 630 g of crude 3,7,11-trimethyl-1,6-dodecadien-3-ol. Analysis by gas chromatography (column: DC-550, available from Gasukuro Kogyo Inc.; column length: 3 m; column temperature: 160° C.; and column: PEG-20M, available from Gasukuro Kogyo Inc.; column length: 3 m; column temperature: 190° C.) revealed that the conversion of 3,7,11-trimethyl-6-dodecen-1-yn-3-ol was 95.5%, and the selectivity to 3,7,11-trimethyl-1,6-dodecadien-3-ol was 94.6%.

To 630 g of the crude 3,7,11-trimethyl-1,6-dodecadien-3-ol thus obtained, 0.16 g of a methanolic sodium methoxide (concentration: 28%) was added, then the resulting mixture was heated at 150° C. for 1 hour to decompose unreacted 3,7,11-trimethyl-6-dodecen-1-yn-3-ol. Thereafter, the resultant solution was simple distilled under a pressure of 7 to 12 mmHg to collect 520 g of a fraction having a boiling point of 120 to 135° C. Analysis by gas chromatography (column: DC-550, available from Gasukuro Kogyo Inc.; column length: 3 m; column temperature: 160° C.) revealed that this fraction contained 93.7% of 3,7,11-trimethyl-1,6-dodecadien-3-ol (yield on the basis of 6,10-dimethyl-5-undecen-2-one: 78.0%).

(Step (f))

A three-necked flask made of glass, equipped with a reflux condenser and having an internal volume of 2 liters, was charged with 520 g (2.17 moles) of the 3,7,11-trimethyl-1,6-dodecadien-3-ol obtained in the step (e), 1.56 g (15 mmols) of triethylamine and 3.95 g (19 mmols) of aluminum isopropoxide. The resulting mixture was heated to 70 to 80° C., then 189.7 g (2.258 moles) of diketene was added dropwise to the mixture over a period of 1.1 hours, and the reaction was carried out for further 1 hour. Thereafter, the temperature of the reaction mixture was raised to 170° C. to carry out the reaction for further 3 hours. Thus, 590 of a reaction mixture (crude 6,10,14-trimethyl-5,9-pentadecadien-2-one) was obtained. Analysis by gas chromatography (column: DC-550, available from Gasukuro Kogyo Inc.; column length: 3 m; column temperature: 210° C.) revealed that the conversion of 3,7,11-trimethyl-1,6-dodecadien-3-ol was 89.1%.

Under a pressure of 0.3 mmHg, 590 g of the reaction mixture (crude 6,10,14-trimethyl-5,9-pentadecadien-2-one) thus obtained was simple distilled to collect 440 g of a fraction having a boiling point of about 110° C. The fraction obtained was purified by distillation to give 360 g of 6,10,14-trimethyl-5,9-pentadecadien-2-one (boiling point: 113° C./0.1 mmHg, purity: 99.2% (yield: 62.7%)).

(Step (g))

An autoclave having an internal volume of 300 ml was charged with 120 g (453.8 mmols) of the 6,10,14-trimethyl-5,9-pentadecadien-2-one obtained in the step (f) and 0.1 g of 10% palladium on carbon to carry out the hydrogenation for 4 hours under hydrogen pressure of 20 kg/cm$^2$ (gauge pressure) at a temperature of 180° C. Thereafter, the catalyst was filtered off to obtain a filtrate. The above procedures for the hydrogenation of 6,10,14-trimethyl-5,9-pentadecadien-2-one were repeated twice (three times in total) to obtain, in total, 340 g of a filtrate. Analysis by gas chromatography (column: DC-550, available from Gasukuro Kogyo Inc.; column length: 3 m; column temperature: 220° C.) revealed that this filtrate was phyton (6,10,14-trimethylpentadecan-2-one) with a purity of 98.4%.

Example 4

(Step (h))

An autoclave having an internal volume of 3 liters was charged with 24.9 g (178 mmols in terms of KOH) of aqueous 40% potassium hydroxide, 1.1 kg (64.7 moles) of liquid ammonia and 0.15 kg (6.25 moles) of acetylene. Thereafter, keeping the temperature inside the autoclave at 4 to 6° C., 340.0 g (1.246 moles) of the phyton obtained in Example 3, i.e., 6,10,14-trimethylpentadecan-2-one, was introduced into the autoclave to initiate the ethynylation.

The ethynylation was carried out at 4 to 6° C. for 2.5 hours, and then 56.3 g of aqueous 25% ammonium sulfate was introduced into the autoclave to stop the reaction. Thereafter, ammonia was purged off from the autoclave while gradually raising the temperature inside the autoclave to room temperature.

Next, 330 g of hexane and 500 g of water were added to the autoclave. A hexane solution containing 3,7,11,15-tetramethyl-1-hexadecyn-3-ol was obtained by collecting the organic layer, followed by washing with water. From this hexane solution, the hexane was removed with a rotary evaporator to give 370 g of crude 3,7,11,15-tetramethyl-1-hexadecyn-3-ol. Analysis by gas chromatography (column: PEG-20M, available from Gasukuro Kogyo Inc.; column length: 3 m; column temperature: 220° C.) revealed that the conversion of phyton was 95.4%.

An autoclave having an internal volume of 300 ml was charged with 93.4 g of the crude 3,7,11,15-tetramethyl-1-hexadecyn-3-ol thus obtained, 55.6 g of hexane and 0.12 g of a Lindlar catalyst (supported on calcium carbonate) to carry out the hydrogenation for 8 hours under hydrogen pressure of 3 to 4 kg/cm$^2$ (gauge pressure) at a temperature of 30 to 60° C. The above procedures for the hydrogenation of 3,7,11,15-tetramethyl-1-hexadecyn-3-ol were repeated twice (three times in total) to carry out the hydrogenation of 246.8 g of 3,7,11,15-tetramethyl-1-hexadecyn-3-ol in total.

The reaction mixtures obtained were combined, and the catalyst was filtered off. From the resultant filtrate, the hexane was removed with a rotary evaporator to give 262.8 g of crude 3,7,11,15-tetramethyl-1-hexadecen-3-ol, i.e., isophytol. Analysis by gas chromatography (column: DC-550, available from Gasukuro Kogyo Inc.; column length: 3 m; column temperature: 215° C.; and column: PEG-20M, available from Gasukuro Kogyo Inc.; column length: 3 m; column temperature: 200° C.) revealed that the conversion of 3,7,11,15-tetramethyl-1-hexadecyn -3-ol was 100%.

To 262.8 g of the crude isophytol thus obtained, 0.06 g of a methanolic sodium methoxide (concentration: 28%) was added, then the resulting mixture was heated at 150° C. for 1 hour to decompose unreacted 3,7,11,15-tetramethyl-1-hexadecyn-3-ol. Thereafter, the resultant solution was simple distilled under a pressure of 0.5 to 0.7 mmHg to collect 208.7 g of a fraction having a boiling point of 103 to 135° C. Analysis by gas chromatography under the same conditions as the above to revealed that this fraction contained 186.3 % of isophytol (yield on the basis of phyton: 75.7%). This fraction was further purified by distillation to give 124.4 g of isophytol (boiling point: 115–120° C./0.15–0.2 mmHg). Analysis by gas chromatography (column: FFAP, available from Gasukuro Kogyo Inc.; column length: 4 m; column temperature: 195° C.) revealed that the isophytol thus obtained had a purity of 99.0%.

Example 5

An autoclave made of stainless steel, equipped with a stirrer and having an internal volume of 5 liters, was charged with 732.1 g (12.6 moles) of acetone and 3.1 g of 10% palladium carbon (a hydrogenation catalyst) in an atmosphere of nitrogen. The temperature inside the autoclave was raised to 115° C., then the pressure inside the autoclave reached 4 kg/cm (gauge pressure).

Thereafter, hydrogen was introduced into the autoclave to adjust the pressure inside the autoclave at 7 kg/cm$^2$ (gauge pressure) (pressure of hydrogen: 3 kg/cm$^2$). Subsequently, 360.0 g (0.18 mole in terms of NaOH) of aqueous 2% sodium hydroxide and 1,033.2 g (12.0 moles) of isovaleraldehyde were each continuously added over a period of 3 hours by means of a feed pump. During the addition, the temperature of the reaction mixture was kept at 110 to 120° C. and also the hydrogen was supplied to keep the pressure inside the autoclave at 7 kg/cm$^2$ (gauge pressure). After the addition of the aqueous sodium hydroxide and isovaleraldehyde was completed, the reaction mixture was kept at temperatures within the above range and stirred for 1.5 hours to run the reaction to the completion.

After cooling to the room temperature, the reaction mixture was filtered to remove the palladium on carbon. Thereafter, the resultant filtrate was stood to separate into two layers, then the organic layer was collected and analyzed by gas chromatography (column: Silicon DC QF1, available from Gasukuro Kogyo Inc.; column temperature: raised from 60 to 200° C.; rate of temperature rise: 5° C./min.) to reveal that 1,339.6 g (yield on the basis of isovaleraldehyde: 87.1%) of 6-methyl-2-heptanone was contained in 1,517.3 g of the organic layer. The conversion of isovaleraldehyde was 97.9%, and the selectivity to 6-methyl-2-heptanone was 89.0%.

1,517,3 g of the organic layer thus obtained was distilled under a reduced pressure to give 1,260.5 g of 6-methyl-2-heptanone (b.p.: 103° C./100 mmHg)

Example 6

An autoclave made of glass, equipped with a stirred and having an internal volume of 1 liter, was charged with 122.0 g (2.1 moles) of acetone and 0.50 g of 10% palladium on carbon (a hydrogenation catalyst). Then, the atmosphere inside the autoclave was replaced with hydrogen of 5 kg/cm$^2$ (gauge pressure), and the mixture obtained was heated to 65° C.

Thereafter, 143.0 g (71.5 mmols in terms of NaOH) of aqueous 2% sodium hydroxide and 172.2 g (2.0 moles) of isovaleraldehyde were each continuously added to the autoclave over a period of 3 hours by means of a feed pump. During the addition, the temperature of the reaction mixture was kept at 65 to 66° C. and also the hydrogen was supplied to keep the pressure inside the autoclave at 5 kg/cm$^2$ (gauge pressure). After the addition of the aqueous sodium hydroxide and isovaleraldehyde was completed, the reaction mixture was kept at temperatures within the above range and stirred for 1.5 hours to run the reaction to the completion.

After cooling to the room temperature, the reaction mixture was filtered to remove the palladium on carbon. Thereafter, the resultant filtrate was stood to separate into two layers, then the organic layer was collected, and analyzed by gas chromatography in the same manner as in Example 5 to reveal that 180.4 g (yield on the basis of isovaleraldehyde: 70.4%) of 6-methyl-2-heptanone was contained in 238.7 g of the organic layer. The conversion of isovaleraldehyde was 97.1%, and the selectivity to the 6-methyl-2-heptanone was 72.5%.

238.68 g of the organic layer thus obtained was distilled under a reduced pressure to give 171.3 g of 6-methyl-2-heptanone (b.p.: 103° C./100 mmHg)

Example 7

An autoclave made of glass, equipped with a stirrer and having an internal volume of 1 liter, was charged with 5.9 g (1.65 moles) of acetone and 0.38 g of Raney nickel (a hydrogenation catalyst). Then, the atmosphere inside the autoclave was replaced with hydrogen of 5 kg/cm$^2$ (gauge pressure), and the mixture obtained was heated to 55° C.

Thereafter, 151.8 g (75.8 mmols in terms of NaOH) of aqueous 2% sodium hydroxide and 129.1 g (1.5 moles) of isovaleraldehyde were each continuously added to the autoclave over a period of 3 hours by means of a feed pump. During the addition, the temperature of the reaction mixture was kept at 59 to 61° C. and also the hydrogen was supplied to keep the pressure inside the autoclave at 5 kg/cm$^2$ (gauge pressure). After the addition of the aqueous sodium hydroxide and isovaleraldehyde was completed, the reaction mixture was kept at temperatures within the above range and stirred for 6 hours to run the reaction to the completion.

After cooling to the room temperature, the reaction mixture was filtered to remove the Raney nickel. Thereafter, the resultant filtrate was stood to separate into two layers, then the organic layer was collected and analyzed by gas chromatography in the same manner as in Example 5 to reveal that 113.8 g (yield on the basis of isovaleraldehyde: 59.2%) of 6-methyl-2-heptanone was contained in 166.6 g of the organic layer. The conversion of isovaleraldeheyde was 96.9%, and the selectivity to the 6-methyl-2-heptanone was 61.1%.

Example 8

An autoclave made of stainless steel, equipped with a stirrer and having an internal volume of 300 ml, was charged with 43.6 g (0.75 mole) of acetone, 43.1 g (0.5 moles) of isovaleraldehyde and 50.0 g (25 mmols in terms of NaOH) of aqueous 2% sodium hydroxide, and 0.126 g of 10% palladium on carbon (a hydrogenation catalyst) in an atmosphere of nitrogen. Then, the atmosphere inside the autoclave was replaced with hydrogen of 6 kg/cm$^2$ (gauge pressure). The reaction was conducted for 4 hours while keeping the temperature of the reaction mixture at 60° C. and also supplying the hydrogen to keep the pressure inside the autoclave at 6 kg/cm$^2$ (gauge pressure).

After cooling to the room temperature, the reaction mixture was filtered to remove the palladium on carbon. Thereafter, the resultant filtrate was stood to separate into two layers, then the organic layer was collected, and analyzed by gas chromatography in the same manner as in Example 5 to reveal that 42.1 g (yield on the basis of isovaleraldehyde: 65.8%) of 6-methyl-2-heptanone was contained in 66.9 g of the organic layer. The conversion of isovaleraldehyde was 99.7%, and the selectivity to the 6-methyl-2-heptanone was 66.0%.

Examples 9 to 14

The procedure of Example 5 was repeated to carry out the reaction, except that the isovaleraldehyde was replaced with the aldehydes as shown in Table 1. Each of the aldehydes, acetone, aqueous 2% sodium hydroxide and palladium on carbon were used in the amounts as shown in Table 1, and the reaction was carried out at a temperature of 120° C. under a hydrogen pressure of 7.0 kg/cm$^2$ and for the time as shown in Table 1 [feed time (time for the addition), run time (time for the further stirring after the addition)].

As the result, 6-methyl-2-heptanone analogues were obtained in the yields as shown in Table 2.

TABLE 1

| | | Aldehyde compound | | Acetone | 2% NaOH aq. | Pd/C | Reaction time | |
|---|---|---|---|---|---|---|---|---|
| Example: | Kind | | Amount [g(mole)] | Amount [g(mole)] | Amount [g(mole)] | Amount (g) | Feed time (hr) | Run time (hr) |
| 9 | Senecioaldehyde | | 150.0(1.8) | 108.8(1.9) | 178.0(0.059) | 0.300 | 2.5 | 1.5 |
| 10 | Tetrahydrocitral | | 109.2(0.7) | 81.3(1.4) | 70.0(0.035) | 0.218 | 3.0 | 8.0 |
| 11 | Citronellal | | 107.8(0.7) | 81.3(1.4) | 70.0(0.035) | 0.431 | 3.0 | 10.0 |
| 12 | Citral | | 112.0(0.7) | 81.3(1.4) | 70.0(0.035) | 0.448 | 3.5 | 13.0 |
| 13 | Hexahydrofarnesal | | 113.0(0.5) | 87.2(1.5) | 50.0(0.025) | 0.452 | 3.5 | 4.0 |
| 14 | Farnesal | | 110.0(0.5) | 87.2(1.5) | 50.0(0.025) | 0.440 | 3.0 | 13.0 |

TABLE 2

| Example: | Product (6-methyl-2-heptanone analogue) | Yield (%) |
|---|---|---|
| 9 | 6-methyl-2-heptanone | 68.5 |
| 10 | 6,10-dimethyl-2-undecanone | 76.9 |
| 11 | 6,10-dimethyl-2-undecanone | 76.4 |
| 12 | 6,10-dimethyl-2-undecanone | 71.5 |
| 13 | 6,10,14-trimethylpentadecan-2-one (phyton) | 60.9 |
| 14 | 6,10,14-trimethylpentadecan-2-one (phyton) | 67.4 |

Example 15

The procedure of steps (c) to (g) of Example 3 was repeated except that, in the step (c) thereof, the 6-methyl-2-heptanone was replaced with the 6-methyl-2-heptanone obtained in Example 5. As the result, phyton was obtained in the same yield as in Example 3.

Example 16

The procedure of Example 4 was repeated except that the phyton obtained in Example 15 was used. As the result, isophytol was obtained in the same yield as in Example 4.

Example 17

The procedure of steps (e) to (g) of Example 3 was repeated except that, in the step (e) thereof, the 6,10-dimethyl-5-undece-2-one was replaced with the 6,10-dimethyl-2-undecanone obtained in Example 10. As the result, phyton was obtained in the same yield as in Example 3.

Example 18

The procedure of Example 4 was repeated except that the phyton obtained in Example 17 was used. As the result, isophytol was obtained in the same yield as in Example 4.

Example 19

The procedure of Example 4 was repeated except that the phyton obtained in Example 14 was used. As the result, isophytol was obtained in the same yield as in Example 4.

What is claimed is:

1. A process for producing a 6-methyl-2-heptanone analogue represented by Formula (1):

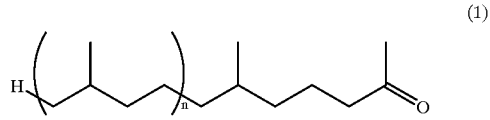

(1)

wherein n is an integer of 0 or 1 or more;
said process comprising the step of allowing hydrogen, acetone and an aldehyde represented by Formula (2):

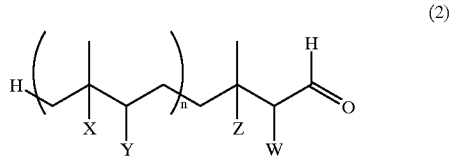

(2)

wherein n is as defined above; X and Y each represents a hydrogen atom or they are coupled together to form a carbon-carbon bond; and Z and W each represents a hydrogen atom or they are coupled together to form a carbon-carbon bond;
to react in one pot in the presence of an aqueous alkali containing an alkaline substance, and a hydrogenation catalyst.

2. The process according to claim 1, wherein said aldehyde of Formula (2) and said aqueous alkali are made to contact with hydrogen gas while each continuously adding the aldehyde and the aqueous alkali in a suspension of the hydrogenation catalyst in the acetone.

3. The process according to claim 1, wherein said alkaline substance is at least one of an alkali metal hydroxide and an an alkaline earth metal hydroxide.

4. The process according to claim 1, wherein said alkaline substance is used in an amount of from 0.001 mole to 0.2 mole per mole of the aldehyde of Formula (2).

5. The process according to claim 1, wherein said alkaline substance is used in an amount of from 0.01 mole to 0.1 mole per mole of the aldehyde of Formula (2).

6. The process according to claim 1, wherein said acetone is used in an amount of from 0.8 mole to 2 moles per mole of the aldehyde of Formula (2).

7. The process according to claim 1, wherein said acetone is used in an amount of from 0.9 mole to 1.2 moles per mole of the aldehyde of Formula (2).

8. The process according to claim 1, wherein the reaction is carried out at a temperature of from 40° C. to 140° C.

9. The process according to claim 1, wherein said hydrogenation catalyst is palladium on carbon, palladium on alumina, Raney nickel or platinum on carbon.

10. The process according to claim 1, wherein said hydrogenation catalyst is used in an amount of from 0.01 10% by weight based on the aldehyde of Formula (2).

11. The process according to claim 1, wherein, in Formulas (1) and (2), n is 0, 1 or 2.

12. The process according to claim 1, wherein at least one of senecioaldehyde and isovaleraldehyde is used as the aldehyde of Formula (2) and 6-methyl-2-heptanone (n is 0) is obtained as the compound of Formula (1).

13. The process according to claim 1, wherein at least one of citral, citronellal and tetrahydrocitral is used as the aldehyde of Formula (2) and 6,10-dimethyl-2-undecanone (n is 1) is obtained as the compound of Formula (1).

14. The process according to claim 1, wherein an aldehyde of the Formula (2) where n is 2 is used as the aldehyde of Formula (2) and phyton (n is 2) is obtained as the compound of Formula (1).

15. The process according to claim 14, wherein the aldehyde of Formula (2) is at least one of farnesal and hexahydrofarnesal.

* * * * *